US005891686A

United States Patent [19]
Dennis et al.

[11] Patent Number: 5,891,686
[45] Date of Patent: Apr. 6, 1999

[54] METHOD OF PRODUCTION OF POLY-β-HYDROXYALKANOATE COPOLYMERS

[75] Inventors: Douglas E. Dennis, Weyers Cave, Va.; Steven C. Slater, Cambridge, Mass.; Ho Gun Rhie, Seoul, Rep. of Korea

[73] Assignee: Center for Innovative Technology, Harrisonburg, Va.

[21] Appl. No.: 881,562

[22] Filed: Jun. 24, 1997

Related U.S. Application Data

[63] Continuation of Ser. No. 610,804, Mar. 7, 1996, which is a continuation of Ser. No. 42,236, Mar. 31, 1993, abandoned, which is a continuation of Ser. No. 35,433, Mar. 24, 1993, Pat. No. 5,569,595.

[51] Int. Cl.$^6$ .................................................. C12P 7/62
[52] U.S. Cl. ................ 435/135; 425/252.7; 425/252.34; 425/252.35
[58] Field of Search ............................. 435/135, 252.3, 435/252.34, 252.35

[56] References Cited

U.S. PATENT DOCUMENTS

| | | | |
|---|---|---|---|
| 4,237,224 | 12/1980 | Cohen et al. | 435/68 |
| 4,336,334 | 6/1982 | Powell et al. | 435/146 |
| 4,396,763 | 8/1983 | Tsuchiya et al. | 536/123 |
| 4,433,053 | 2/1984 | Hughes et al. | 435/141 |
| 4,634,678 | 1/1987 | Salstrom et al. | 435/317 |
| 4,743,453 | 5/1988 | Ahern et al. | 426/41 |
| 4,760,022 | 7/1988 | Molin et al. | 435/320 |
| 4,806,471 | 2/1989 | Molin et al. | 435/68 |
| 4,806,480 | 2/1989 | Lopez | 435/252.33 |
| 4,876,331 | 10/1989 | Doi | 528/361 |
| 4,950,749 | 8/1990 | Johal et al. | 536/127 |
| 5,017,692 | 5/1991 | Zurawski et al. | 530/351 |
| 5,229,279 | 7/1993 | Peoples et al. | 435/135 |
| 5,240,837 | 8/1993 | Tomich et al. | 435/172.3 |
| 5,244,806 | 9/1993 | Bang et al. | 435/252.33 |
| 5,245,023 | 9/1993 | Peoples et al. | 536/23.2 |
| 5,250,430 | 10/1993 | Peoples et al. | 435/232 |
| 5,334,520 | 8/1994 | Dennis | 435/136 |
| 5,395,927 | 3/1995 | Böck et al. | 536/23.2 |

FOREIGN PATENT DOCUMENTS

| | | |
|---|---|---|
| 069 497 A2 | 1/1983 | European Pat. Off. . |
| 136 829 A2 | 4/1985 | European Pat. Off. . |
| 155 189 A2 | 9/1985 | European Pat. Off. . |
| 204 442 A2 | 12/1986 | European Pat. Off. . |
| 4003827 A1 | 8/1991 | Germany . |
| WO 89/00202 | 1/1989 | WIPO . |
| WO 91/00917 | 1/1991 | WIPO . |
| WO 91/18993 | 12/1991 | WIPO . |
| WO 93/06225 | 4/1993 | WIPO . |
| WO 93/24633 | 12/1993 | WIPO . |

OTHER PUBLICATIONS

Peoples and Sinskey, "Genes to PHA Polymers," *International Symposium on Biodegradable Polymers:* p. 108, Oct. 29–31, 1991.

Steinbüchel and Schlegel, "Physiology and molecular genetics of poly(β–hydroxyalkonoic acid) synthesis in *Alcaligenes eutrophus*," *Molecular Microbiology* 5(3); 535–542, 1991.

Fidler and Dennis, "Polyhydroxyalkanoate production in recombinant *Escherichia coli*," *FEMS Microbiology Reviews 103:* 231–236, 1992.

Jenkins and Nunn, "Regulation of the ato Operon bt the atoC Gene in *Escherichia coli*," *Journal of Bacteriology 169*(5): 2096–2102, 1987.

Johnson et al., "Induction Studies on the Poly–β–Hydroxybutyrate Biosynthetic Pathway in *Alcaligenes eutrophus* H16 and in *Excherichia coli*," *Virginia Journal of Science:* 150, 1987.

Maloy and Nunn, "Role of Gene fadR in *Escherichia coli* Acetate Metabolism," *Journal of Bacteriology 148*(1): 83–90, 1981.

Slater and Dennis, "Cloning and Expression of the *Alcaligenes eutrophus* H16 Beta Ketothiolase Gene in *Escherichia coli*," *American Society for Microbiology, Annual Meeting*, Abst. #H–123, Mar. 1–6, 1987.

Slater et al., "Cloning of the *Alcaligenes eutrophus* H16 Poly–β–Hydroxybutyrate Biosynthetic Pathway into *Escherichia coli*, " *Virginia Journal of Science:*152, 1987.

Slater et al., "Production of Poly–(3–Hydroxybutyrate–Co–3–Hydroxyvalerate) in a Recombinant *Escherichis coli* Strain," *Applied Env. Microbiology 58*(4): 1089–1094, 1992.

Van Dyk and LaRossa, "Involvement of ack–pta operon products in α–ketobutyrate metabolism by *Salmonella typhimurium*," *Mol. Gen. Genet. 207:* 435–440, 1987.

Anderson et al., "Production of SHMT in *Klebsiella aerogenes*," *188th ACS National Meeting:* Section MBTD, Abstract #70, 1984.

Ayers et al., eds., *Microbiology of Foods*, W.M. Freeman & Co., San Fran., pp. 191–192, 1980.

Ballard et al., "Formation of Polymers of β–Hydroxybutyric Acid in Bacterial Cells and a Comparison of the Morphology of Growth With the Formation of Polyethylene in the Solid State," *Recent Advances in Mechanistic and Synthetic Aspects of Polymerization:* 293–314, D.Reidel Publishing Company, 1987.

(List continued on next page.)

*Primary Examiner*—Charles L. Patterson, Jr.
*Attorney, Agent, or Firm*—Seed & Berry LLP

[57] ABSTRACT

The present invention provides methods for the production of poly-β-hydroxyalkanoate copolymer comprising the steps of (a) introducing into a prokaryotic host cell a vector construct which directs the expression of a sequence which encodes a poly-β-hydroxybutyrate biosynthetic pathway, (b) introducing into the host cell a vector construct which directs the expression of one or more proteins which regulate acetate and propionate metabolism, (c) culturing the host cell in medium containing propionate or a derivative thereof, and (d) isolating poly-β-hydroxyalkanoate copolymer from the cultured host cell.

14 Claims, 29 Drawing Sheets

OTHER PUBLICATIONS

Borel et al., "In vivo overexpression and purification of *Escherichia coli* tRNA$^{ser}$," *FEBS 324*(2): 162–166, 1993.

Brown et al., "The Enzymic Interconversion of Acetate and Acetyl–coenzyme A in *Escherichia coli*," *Journal of General Microbiology 102:* 327–336, 1977.

Byrom, D., "Polymer synthesis by microorganisms: technology and economics," *Trends in Biotechnology 5:* 246–250, 1987.

DeBoer et al., "The tac promoter: A functional hybrid derived form the trp and lac promoters," *Proc. Natl. Acad. Sci. USA 80:* 21–25, 1983.

Gerdes, K., "The PARB (HOK/SOK) Locus of Plasmid R1: A General Purpose Stabilization System," *Biotechnology 6:* 1402–1405, 1988.

Hardesty et al., "Deletion Analysis of Sucrose Metabolic Genes form a Salmonella Plasmid Cloned in *Escherichia coli* K12," *Plasmid 18:* 142–155, 1987.

Harrison, S., "Bacteria Cell Disruption: A Key Unit Operation in the Recovery of Intracellular Products," *Biotechnology Advances 9*(2), 217–240, 1991.

Icho, T., "Membrane–Bound Phosphatases in *Escherichia coli:* Sequence of the pgpB Gene and Dual Subcellular Localization of the pgpB Product," *Journal of Bacteriology 170*(11): 5117–5124, 1988.

Janes et al., "Molecular Characterization of the Poly–β–Hydoxybutyrate Biosynthetic Pathway of *Alcaligenes eutrophus* H16," *Novel Biodegradable Microbial Polymers*(E.A. Dawes Ed.). pp. 175–190, 1990.

Kalousek et al., "Release of Poly–β–hydroxybutyrate Granules from *Escherichia coli* by Protein E–mediated Lysis," *International Symposium on Biodegradable Polymers:* p. 150, Oct. 29–31, 1991.

Kleiner et al., "Construction of Multicopy Expression Vectors for Regulated Over–production of Proteins in *Klebsiella pneumoniae* and Other Enteric Bacteria," *Journal of General Microbiology 134:* 1779–1784, 1988.

Liebergesell and Steinbüchel, "Cloning and nucleotide sequences of genes relvant for biosynthesis of poly(3–hydroxybutyric acid) in *Chromatium vinosum* strain D," *European Journal of Biochemistry 209*(1): 135–150, 1992.

Nomura et al., "Construction of expression plasmids producing high levels of human immuno interferon in *E. coli*," *Nucleic Acids Research, Symposium Series 12:* 87–90, 1983.

Old and Primrose, eds. *Principles of Gene Manipulation: An Introduction to Genetic Engineering* 4th ed., Blackwell Scientific Publications, 1989, pp. 59, 153–160, 164–167.

Peoples and Sinskey, "Fine structural analysis of the *Zoogloea ramigera* phbA–phbB locus encoding β–ketothiolase and acetoacetyl–CoA reductase: nucleotide sequence of phbB," *Molec. Microbio. 3:* 349–357, 1989.

Peoples and Sinskey, "Poly–β–hydroxybutyrate Biosynthesis in *Alcaligenes eutrophus* H16: Characterization of the Genes Encoding β–Ketothiolase and Acetoacetyl–CoA Reductase," *Journal of Biological Chemistry 264*(26): 15293–15297, 1989.

Peoples and Sinskey, "Poly–β–hydroxybutyrate (PHB) Biosynthesis in *Alcaligenes eutrophus* H16: Indentification and Characterization of the PHB Polymerase Gene (phbC)," *Journal of Biological Chemistry 264:* 15298–15303, 1989.

Peoples et al., "Biosynthetic Thiolase from *Zoogloea ramigera*," *Journal of Biological Chemistry 262:* 97–102, 1987.

Ploux et al., "The NADPH–linked acetoacetyl–CoA reductase from *Zoogloea ramigera:* Characterization and mechanistic studies of the cloned enzyme over–produced in *Escherichia coli*," *European Journal of Biochemistry 174:* 177–182, 1988.

Russell and Bennett, "Construction and analysis of in vivo activity of *E. coli* promoter hybrids and promoter mutants that alter the –35 to –10 spacing," *Gene 20:* 231–243, 1982.

Sambrook et al., eds., *Molecular Cloning: A Laboratory Manual,* 2nd ed., Cold Spring Harbor Laboratory Press, 1989, pp. 17.12–17.13, 17.17–17.21,17.27.

Schubert et al., "Cloning of the *Alcaligenes eutrophus* Genes for Synthesis of Poly–β–Hydroxybutyric Acid (PHB) and Synthesis of PHB in *Escherichia coli*," *Journal of Bacteriology 170:* 5837–5847, 1988.

Schubert et al., "Molecular Analysis of the *Alcaligenes eutrophus* Poly(3–Hydroxybutyrate) Biosynthetic Operon: Identification of the N Terminus of Poly(3–Hydroxybutyrate) Synthase and Identification of the Promoter," *Journal of Bacteriology 173:* 168–175, 1991.

Slater et al., "Cloning and Expression in *Escherichia coli* of *Alcaligenes eutrophus* H16 Poly–β–Hydroxybutyrate Biosynthetic Pathway," *Journal of Bacteriology 170*(10): 4431–4436, 1988.

Studier et al., "Use of T7 RNA Polymerase to Direct Expression of Cloned Genes," *Methods in Enzymology 185:* 60–89, 1990.

Togna et al., "Effects of Plasmid Copy Number and Runaway Plasmid Replication on Overproduction and Excretion of β–Lactamase from *Escherichis coli*," *Biotechnology Progress 9:* 31–39, 1993.

Tsunekawa et al., "Acquisition of a Sucrose Utilization System in *Escherichia coli* K–12 Derivatives and Its Application to Industry," *Applied and Environmental Microbiology 58*(6): 2081–2088, 1992.

Watson et al., eds., *Molecular Biology of the Gene,* 4th ed. Benjamin/Cummings Publishing Co. Menlo Park, CA, p. 437, 1987.

Analysis of cosmid clones for enzyme activity and PHB accumulation

| Bacterium[a] | Cosmid | β-Ketothiolase activity[b] | Acetoacetyl-CoA reductase activity[c] | mg of PHB/ml of culture | %PHB |
|---|---|---|---|---|---|
| E. coli LE392 | None | 0.0 | 0.0 | 0.0 | 0 |
| A. eutrophus H16 | None | 12.4 | 12.3 | 1.18 | 35 |
| E. coli LE392 | pAE65 | 5.2 | 39.0 | 0.03 | 1 |
| E. coli LE392 | pAE175 | 16.2 | 0.2 | 0.47 | 16 |
| E. coli LE392 | pAE537 | 2.4 | 0.0 | 0.0 | 0 |
| E. coli LE392 | pAE683 | 10.4 | 0.0 | 0.0 | 0 |
| E. coli LE392 | pAE689 | 14.8 | 0.2 | 0.64 | 20 |
| E. coli LE392 | pAE902 | 8.5 | 0.0 | 0.0 | 0 |

[a] Bacteria were grown in LB plus 1% gluconate
[b] Micromoles of acetoacetyl-CoA degraded per minute per milligram of protein.
[c] Micromoles of NADPH reduced per minute per milligram of protein.

Fig. 2

Analysis of subclones for enzyme activity and PHB production

| Bacterium[a] | Plasmid | β-Ketothiolase activity[b] | Acetoacetyl-CoA reductase activity[c] | mg of PHB/ml of culture | %PHB |
|---|---|---|---|---|---|
| E. coli LE392 | None | 0.0 | 0.0 | 0.0 | 0 |
| A. eutrophus H16 | None | 3.5 | 11.2 | 1.64 | 49 |
| E. coli LE392 | pAE175 | 1.7 | 1.2 | 0.71 | 19 |
| E. coli DH5 | pBK6 | 1.6 | 0.0 | 0.0 | 0 |
| E. coli DH5 | pBK12 | 2.0 | 4.5 | 0.71 | 18 |
| E. coli DH5 | pSB2 | 0.0 | 0.0 | 0.0 | 0 |
| E. coli DH5 | pSB3 | 0.0 | 0.0 | 0.0 | 0 |
| E. coli DH5 | pSB8 | 59.2 | 50.1 | 0.0 | 0 |
| E. coli DH5 | pSB9 | 20.2 | 8.7 | 0.0 | 0 |
| E. coli DH5 | pSB13 | 0.0 | 0.0 | 0.0 | 0 |
| E. coli DH5 | pSB14 | 0.0 | 0.0 | 0.0 | 0 |
| E. coli DH5 | pSB20 | 2.7 | 0.7 | 2.82 | 54 |
| E. coli DH5 | pSB21 | 2.4 | 0.6 | 2.28 | 39 |

[a] For enzyme assays, bacteria were grown in LB. For the PHB assay, bacteria were grown in LB plus 1% gluconate.
[b] Micromoles of acetoacetyl-CoA degraded per minute per milligram of protein.
[c] Micromoles of NADPH reduced per minute per milligram of protein.

*Fig. 4*

| Strain | Medium | OD-600 | PHB | PHV |
|---|---|---|---|---|
| 5218 | 40 mM Ac/10 mM Prop | 2.62 | 0 | 0 |
| 5218 | 40 mM Ac/10 mM Prop/0.4% glu | 8.18 | 292,000 | 31,000 |
| 5218 | 20 mM Ac/25 mM Prop/0.4% glu | 7.46 | 169,000 | 64,000 |
| 5218 | 10 mM Ac/10 mM Prop/0.4% glu | 6.28 | 77,000 | 52,000 |
| 5218 | 25 mM Ac/0.4% glu | 8.02 | 327,000 | 0 |
| 5218 | 25 mM Prop/0.4% glu | 5.88 | 99,000 | 63,000 |
| HMS174/p4A | 20 mM Ac/25 mM Prop/0.4% glu | 5.56 | 120,000 | 0 |
| HMS174/p4A | 25 mM Prop/0.4% glu | 3.46 | 14,000 | 0 |

Fig. 11

Small arrows represent regulation

Effect of AckA-pta pathway on 3-HV content

| E. coli strain | Activity[a] | | | | | | Mol % 3-HV |
|---|---|---|---|---|---|---|---|
| | Acetate Kinase | Phosphotrans acetylase | Acetyl-CoA Synthetase | Propionyl-CoA Synthetase | 3-Hβ[b] | 3-HV | |
| K12 (pJM9131) | .095 | 4.15 | 0.2 | 0.01 | 0.29 | 0.006 | 2.0 |
| LS5218 (pJM9131) | 1.70 | 4.42 | 0.46 | 0.01 | 0.28 | 0.03 | 10.7 |
| JMU222 (pJM9131) | 0.02 | 2.57 | 0.002 | 0.004 | 0.28 | 0.004 | 1.4 |
| JMU210 (pJM9131) | 0.82 | { } | 0.001 | 0.001 | 0.25 | 0.008 | 3.0 |
| JMU209 (pJM9131) | 0.01 | { } | 0.002 | 0.003 | 0.39 | 0.007 | 1.8 |

[a] Activities of acetate kinase and Phosphotransacetylase are expressed as umol Hydroxamate or NADH formed per minute per mg protein.
Activities of acetyl-CoA synthase and propionyl-CoA synthetase are given in nmol of substrate incorporated into product formed per minute per mg protein.
[b] Milligrams of polymer per mg cell dry weight.

*Fig. 18*

Elevation of 3-HV content by overproduction of acetate kinase

| E. coli strain | Activity[a] | | | | | | Mol % 3-HV |
|---|---|---|---|---|---|---|---|
| | Acetate Kinase | Phosphotrans acetylase | Acetyl-CoA Synthetase | Propionyl-CoA Synthetase | 3-Hβ[b] | 3-HV | |
| JMU222 (pJM9350) | 40.3 | 5.65 | 0.27 | 0.07 | 0.17 | 0.05 | 22.8 |
| JMU209 (pJM9350) | 57.8 | ( ) | 0.008 | 0.008 | 0.27 | 0.008 | 2.8 |
| LS5218 (pJM9350) | 49.0 | 2.77 | 0.12 | 0.06 | 0.22 | 0.08 | 26.7 |

[a]Activities of acetate kinase and phosphotransacetylase are expressed as umol hydroxamate or NADH formed per minute per mg protein.
Activities of acetyl-CoA synthetase and propionyl-CoA synthetase are given in nmol of substrate incorporated into CoA product formed per minute per mg protein.
[b]Milligrams of polymer per mg cell dry weight.

Fig. 19

Effect of structural proteins of ato operon on [$^{14}$C] propionate uptake and 3-HV content

| Strain | Specific Uptake[a] | HB[b] | HV[b] | Mol % 3-HV |
|---|---|---|---|---|
| K12 | 0.0022 | 0.293 | 0.003 | 1.0 |
| atoC | 0.0256 | 0.225 | 0.025 | 10.0 |
| atoC atoA | 0.0122 | 0.181 | 0.029 | 13.2 |
| atoC atoD | 0.0022 | 0.163 | 0.007 | 4.1 |

[a]Specific uptake is expressed in nanomoles per minute per weight.
[b]Milligrams of polymer per mg cell dry weight.

Fig. 24

| Mutation | HB(GC counts) | HV(GC counts) | mol%HV |
| --- | --- | --- | --- |
| fadR | 306115 | 83192 | 21.0% |
| fadR fadL | 594793 | 64275 | 9.7% |
| fadR fadB | 74679 | 0 | 0% |
| fadR fadA | 174790 | 0 | 0% |

*Fig. 28*

METHOD OF PRODUCTION OF POLY-β-HYDROXYALKANOATE COPOLYMERS

CROSS-REFERENCE TO RELATED APPLICATIONS

This application is a continuation of U.S. patent application Ser. No. 08/610,804, filed Mar. 7, 1996, which is a continuation of U.S. patent application Ser. No. 08/042,236, filed Mar. 31, 1993 and now abandoned, which is a continuation of U.S. patent application Ser. No. 08/035,433, filed Mar. 24, 1993 and issued on Oct. 29, 1996 as U.S. Pat. No. 5,569,595.

TECHNICAL FIELD

The present invention relates generally to the production of polymers in prokaryotic host cells, and more specifically, to the production of poly-β-hydroxyalkanoates.

BACKGROUND OF THE INVENTION

Poly-β-hydroxybutyrate "PHB" is a naturally occurring bacterial polyester that was discovered by Lemoigne in 1926 (Lemoigne, *Bull. Soc. Chim. Biol.* 8:770, 1926). PHB is believed to exist as a bacterial energy storage compound which is accumulated during times of nutritional stress, and is degraded when the stress is relieved (Oeding et al., *Biochemical Journal* 134:239–248, 1973; Senior et al., *Biochemistry Journal* 134:225–238, 1973). The most remarkable aspect of PHB accumulation is the intracellular levels to which it can accumulate. In *Alcaligenes eutrophus*, PHB levels have been known to reach 80% of the cell dry weight (Oeding et al., *Biochemical Journal* 134:239–248, 1973).

In the early 1950's it was discovered that purified PHB was, in fact, a biodegradable thermoplastic that could be molded or shaped into a variety of items. Its biodegradability is derived from the fact that many bacteria that have the biosynthetic portion of the pathway also contain a biodegradative pathway (Anderson et at., *Microbiological Reviews* 54(4):450–472, 1990). Theoretically, thermoplastic items made from PHB could then be composted in landfills, where they can be degraded by both aerobic and anaerobic bacteria (Winton, *Chemical Week*, 55–57, Aug. 28, 1985). Commercialization efforts were initiated by W. R. Grace, but were halted when it became apparent that there were formidable technical difficulties to be overcome, and public interest in the project was low (Holmes, *Phys. Technology* 16:32, 1985).

PHB research languished until the 1970's, when the laboratories of H. G. Schlegel in Germany and E. A. Dawes in England undertook to elucidate the enzymological mechanism of PHB production. In a series of publications, both laboratories defined the pathway of PHB biosynthesis in Alcaligenes and Azotobacter, (Anderson et al., *Microbiological Reviews* 54(4):450–472, 1990; Jackson et al., *Journal of General Microbiology* 97:303–313, 1976; Oeding et al., *Biochemical Journal* 134:239–248, 1973; Ritchie, *Biochemistry Journal* 121:309–316, 1972; Schlegal et al., *Antonie Van Leeuwenhoek* 32:277, 1966; Senior et al, *Biochemistry Journal* 134:225–238, 1973; Ward et al., *Journal of General Microbiology* 102:61–68, 1977).

In the early 1980's interest in PHB was again stimulated when it was found that PHB is actually part of a family of polyesters, termed poly-β-hydroxyalkanoates (PHAs) (Findlay et al., *Applied and Environmental Microbiology* 45(1):71–78, 1983). Loosely defined, PHAs are a family of polymerized fatty acid esters, in which the fatty acid monomer is normally from 4–10 carbons. PHAs that contain higher carbon-number fatty acids can be made into a more flexible thermoplastic, whereas PHAs containing lower carbon-number fatty acids tend to be more brittle (Byrom, *Trends Biotechnology* 5:246–250, 1987). For example, poly-(3-hydroxybutyrate-co-3-hydroxyvalerate) is much more amenable to plastic film production than poly-3-hydroxybutyrate, which is a brittle plastic.

The environmental and commercial importance of PHAs lies in their potential to reduce the volume of solid waste. Although estimates vary widely, the best data available indicates that 7–10% of all landfill waste is plastic (Beardsley et al., *Scientific American*, 1988). This is the equivalent of millions of pounds of plastic disposed in this manner every day. Since the average life of such plastic can be as long as several hundred years, poly-β-hydroxalkanoates offer distinct environmental advantages (e.g., a 0.07 mm-thick film of PHB degrades in 10 weeks in soil; Doi et al, *Applied and Environmental Microbiology* 55(11):2932–2938, 1989).

Unfortunately, PHA technology has not yet replaced petrochemical-based plastics because of the high cost of production. Currently, PHAs are being marketed for approximately $14 per pound, whereas petroleum-based plastics sell for less than $1 per pound (Winton, *Chemical Week*, 55–57, Aug. 28, 1985). The primary reason for the high cost of poly-β-hydroxyalkanoates is the mode of production: fermentation times are as long as 100 hours, final PHA levels fluctuate, purification procedures are cumbersome and expensive, and substrate costs are inordinately high (Byrom et al., *Trends Biotechnology* 5:246–250, 1987). Therefore, before these plastics can find their way to the commodity marketplace, significant improvements are necessary.

The present invention overcomes previous difficulties of PHA production, and further provides other related advantages.

SUMMARY OF THE INVENTION

The present invention provides methods for the production of poly-β-hydroxyalkanoate copolymer. Briefly, within one aspect of the present invention methods for the production of poly-β-hydroxyalkanoate copolymer are provided comprising the steps of (a) introducing into a prokaryotic host cell a vector construct which directs the expression of a sequence which encodes a polyβ-hydroxybutyrate biosynthetic pathway, (b) introducing into the host cell a vector construct which directs the expression of one or more proteins which regulate acetate and propionate metabolism, (c) culturing the host cell in medium containing propionate or a derivative thereof, and (d) isolating poly-β-hydroxyalkanoate copolymer from the cultured host cell.

Within another aspect of the invention, methods for the production of poly-β-hydroxyalkanoate copolymer are provided comprising the steps of (a) introducing into a prokaryotic host cell a vector construct which directs the co-expression of a sequence which encodes a poly-β-hydroxybutyrate biosynthetic pathway, and one or more proteins which regulate acetate and propionate metabolism, (b) culturing the host cell in medium containing propionate or a derivative thereof, and (c) isolating poly-β-hydroxyalkanoate copolymer from the cultured host cell.

Within yet another aspect of the present invention methods for the production of poly-β-hydroxyalkanoate copolymer are provided comprising the steps of (a) introducing into a prokaryotic host cell which produces poly-β-hydroxybutyrate a vector construct which directs the expression of one or more proteins which regulate acetate and propionate metabolism, (b) culturing the host cell in medium containing propionate or a derivative thereof, and (c) isolating poly-β-hydroxyalkanoate copolymer from the cultured host cell.

Within various embodiments of the present invention, the host cell may be an Enterobacteriaceae host cell or, preferably, an *E. coli* host cell. Within other embodiments, the protein which regulates acetate and propionate metabolism may be encoded by a fadR mutant, an atoC mutant, by ackA, or by pta. In addition, in order to increase expression of PHV, the vector construct may direct the expression of proteins which are encoded by a combination of these genes (e.g., fadR and atoC).

Within other aspects of the invention, a host cell is provided which contains a vector construct which directs the expression of a sequence which encodes a poly-β-hydroxybutyrate biosynthetic pathway, and a vector construct which directs the expression of one or more proteins which regulate acetate and propionate metabolism. Within another aspect, a host cell is provided which contains a vector construct which directs the co-expression of a sequence which encodes a poly-β-hydroxybutyrate biosynthetic pathway, and one or more proteins which regulate acetate and propionate metabolism. Within various embodiments, the host cell is *E. coli*.

These and other aspects of the present invention will become evident upon reference to the following detailed description and attached drawings. In addition, reference is made herein to various publications, which are hereby incorporated by reference in their entirety.

BRIEF DESCRIPTION OF THE DRAWINGS

FIG. 2 is a table containing an analysis of cosmid clones for enzyme activity and PHB accumulation.

FIG. 4 is a table containing an analysis of subclones for enzyme activity and PHB production.

FIG. 11 is a table showing an analysis of PHB/PHV production in varying ratios of acetate:propionate and glucose substrates.

FIG. 18 is a table which provides results on the effect of the ackA pathway on 3-HV content.

FIG. 19 is a table which provides results on the elevation of 3-HV content by overproduction of acetate kinase.

FIG. 24 is a table which provides results on the effect of structural proteins of the ato operon on [$^{14}$C] propionate uptake and 3-HV content

FIG. 28 is a table which provides GC integration units for 3-HB, 3-HV production for fadR, fadR fadL, fadR fadB, and fadR fadA mutations.

DETAILED DESCRIPTION OF THE INVENTION

Figure 1:
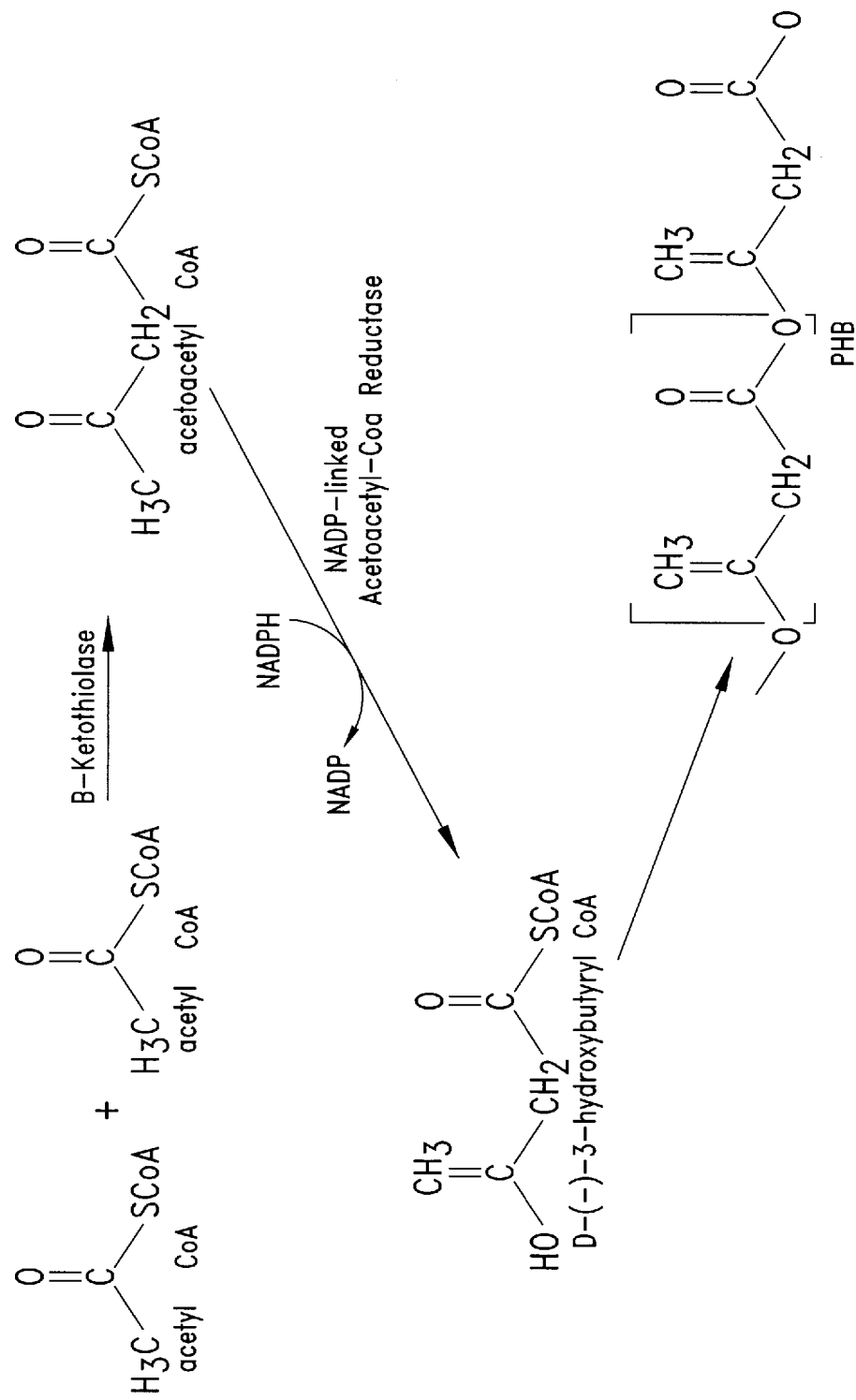
FIG. 1 is a chemical reaction sequence showing the synthesis of PHB.

As noted above, the present invention provides methods for the production of poly-β-hydroxyalkanoate copolymer. Briefly, within one aspect of the present invention methods for the production of poly-β-hydroxyalkanoate copolymer is provided, comprising the steps of (a) introducing into a prokaryotic host cell a vector construct which directs the expression of a sequence which encodes a poly-β-hydroxybutyrate biosynthetic pathway, (b) introducing into the host cell a vector construct which directs the expression of one or more proteins which regulate acetate and propionate metabolism, (c) culturing the host cell in medium containing propionate or a derivative thereof, and (d) isolating poly-β-hydroxyalkanoate copolymer from the cultured host cell. Within other aspects of the invention, a method for the production of poly-β-hydroxyalkanoate copolymer is provided comprising the steps of (a) introducing into a prokaryotic host cell a vector construct which directs the co-expression of a sequence which encodes a poly-β-hydroxybutyrate biosynthetic pathway, and one or more proteins which regulate acetate and propionate metabolism, (b) culturing the host cell in medium containing propionate or a derivative thereof, and (c) isolating poly-β-hydroxyalkanoate copolymer from the cultured host cell. Within yet another aspect of the present invention, a method for the production of poly-β-hydroxyalkanoate copolymer is provided comprising the steps of (a) introducing into a prokaryotic host cell which produces poly-β-hydroxybutyrate a vector construct which directs the expression of one or more proteins which regulate acetate and propionate metabolism, (b) culturing the host cell in medium containing propionate or a derivative thereof, and (c) isolating poly-β-hydroxyalkanoate copolymer from the cultured host cell.

Various prokaryotic host cells may be utilized within the context of the present invention for production of the poly-β-hydroxyalkanoate ("PHA") copolymer. Generally, preferred prokaryotic host cells should have a well-characterized genetic system, including known cloning vectors and methods of genetic manipulation. They should also preferably grow well in minimal medium, ideally to a high cell density, and without any special requirements (physical or physiological). Representative examples of such host cells include members of the Bacillaceae, Nocardiaceae, Streptomycetaceae, Pseudomonadaceae, Corynebacteria, and Enterobacteriaceae.

Preferred host cells in the Family Enterobacteriaceae include Escherichia, Citrobacter, Klebsiella, Enterobacter, and Serratia, as well as Zymomonas and Flavobacterium, which are within the Enterobacteriaceae but of uncertain affiliation. Particularly preferred host cells include *E. coli*, *Klebsiella oxytoca*, and *Klebsiella aerogenes*. Preferred host cells in the Family Pseudomonaceae include *P. fluorescens*.

The above-described prokaryotes may be readily obtained from a variety of commercial sources including, for example, the American Type Culture Collection (ATCC) (Rockville, Md.). Alternatively, many of the above-described bacteria may be isolated from sources which are known by those of skill in the art to contain such prokaryotes, based upon techniques which are known in the art (see Bergy's *Shorter Manual of Determinative Bacteriology*, Williams & Wilkins (pub.), John G. Holt (ed.), 8th edition, 1977).

Once a prokaryotic host cell has been obtained, a vector construct which directs the expression of a sequence which encodes a poly-β-hydroxybutyrate biosynthetic pathway is introduced into the host cell. Within the context of the present invention, a vector construct is understood to refer to an assembly which is capable of expressing the sequence(s) of interest. The vector construct must include an origin of replication, and preferably includes a stabilization locus (e.g., the parB locus), and selectable antibiotic resistance markers such as chloramphenicol, kanamycin, or tetracycline resistance genes. In addition, the vector construct may also contain a genetic system that allows control of copy number (e.g. RAPT from Nycomed), a regulatable promoter, as well as a translation termination sequence, and one or more restriction sites.

As noted above, the vector construct is utilized to introduce a sequence which encodes a poly-β-hydroxybutyrate biosynthetic pathway into the host cell. The three step biosynthetic pathway for poly-β-hydroxybutyrate has been found in many prokaryotic organisms, including Azotobacter, Beigerinckia, Alcaligenes, Pseudomonas, Rhizobium, and Rhodospirillum, and has been studied extensively in *A. eutrophus* and *Azotobacter beijerinckii*. Briefly, β-ketothiolase first catalyzes the reversible condensation of two acetyl coenzyme A (CoA) molecules to acetoacetyl-CoA. The acetoacetyl-CoA is then reduced by acetoacetyl-CoA reductase to D-(−)3 hydroxybutyryl-CoA. Enzyme action of the acetoacetyl-CoA reductase is dependent on NADPH. PHB synthetase polymerizes the D-(−)-3-hydroxybutyryl-CoA to poly-β-hydroxybutyrate.

The poly-β-hydroxybutyrate biosynthetic pathway was first cloned from *A. eutrophus* into *E. coli* (see Slater et al., *J. Biol.* 170:4431, 1988; see also U.S. Ser. No. 07/528,549, filed Jun. 7, 1989, and U.S. Ser. No. 071705,806, filed May 24, 1991, all of which are expressly incorporated herein by reference). The cloning of the PHB biosynthetic pathway into *E. coli* has also been later described by Schubert et al., *J. Bacter.* 170:5837, 1988; Peoples, et al., *J. Biol. Chem.* 264:15298, 1989; and Peoples et al., *J. Biol. Chem.* 264:15293, 1989.

Particularly preferred vector constructs which direct the expression of the poly-β-hydroxybutyrate biosynthetic pathway, and which may be utilized within the present invention include pJM8801 (formerly p4A, ATCC Deposit No. 68329), pJM9116 (ATCC Deposit No. 68992), pJM9123 and pJM9131. pJM9123 may be constructed essentially as described by Slater et at. in *Appl. and Env. Micro.* 58(4):1089–1094, 1992. Briefly, pJM9123 was constructed by digesting pJM8801 with restriction endonucleases Dra I and EcoR I. The resulting 6.5 kb fragment carrying the PHB operon and plasmid origin of replication was rendered blunt-ended by using Klenow polymerase with the appropriate reaction conditions. The blunt-ended fragment was subsequently ligated to a 1.6 kb fragment obtained from plasmid pKG1022 by digestion with the restriction endonuclease HincII. This fragment contains the kanamycin resistance gene and the ParB locus (Gerdes, *Bio/Technology* 6:1402–1405, 1988).

Similarly, pJM9131 was constructed by cutting pJM8801 with EcoR I, adding a kanamycin-resistance marker with EcoR I ends (GENBLOCK*, Pharmacia), and religating at EcoR I. Next, the gene for ampicillin resistance was removed by digestion with Dra I, and the plasmid religated. The resulting multi-copy plasmid confered kanamycin resistance, but not ampicillin resistance.

A variety of other vector constructs which are described in co-pending applications U.S. Ser. Nos. 07/890,925 and 07/528,549, (which are expressly incorporated by reference herein) may also be utilized within the context of the present invention. Examples include pJM9101 (ATCC Deposit No. 69000), pJM9113 (ATCC Deposit No. 68989), pJM9114 (ATCC Deposit No. 68990), pJM9115 (ATCC Deposit No. 68991), pJM9117 (ATCC Deposit No. 68993), pJM9118 (ATCC Deposit No. 68994), pJM9119 (ATCC Deposit No. 68995), pJM9120 (ATCC Deposit No. 68996), pJM9125 (ATCC Deposit No. 68998), and pJM9126 (ATCC Deposit No. 68999).

As noted above, within one aspect of the present invention, a vector construct which directs the expression of one or more proteins which regulate acetate and propionate metabolism, is introduced into the host cell. Briefly, as noted above PHB is made by the action of three enzymes, beta-ketothiolase, acetoacetyl-CoA reductase, and PHB synthetase (Andersen, et al, Microbiological Reviews 54, No. 4:450–472; 1990). In the first step of PHB biosynthesis, two acetyl-CoA molecules are condensed to acetoacetyl-CoA by the action of the thiolase. Acetoacetyl-CoA is then reduced to D-(−)-3-hydroxybutyryl CoA by the action of the reductase, followed by polymerization into PHB by the synthetase (FIG. 1). In like manner, PHA [e.g., P(HB-co- HV)] is believed to be made when the first reaction utilizes propionyl-CoA in conjunction with an acetyl-CoA to form an acetopropionyl-CoA molecule, which is subsequently carried through the rest of the pathway. A variety of proteins may be utilized within the context of the present invention to regulate acetate and propionate metabolism. Representative examples include protein encoded by a fadR mutant, protein encoded by an atoC mutant, protein encoded by ackA, and protein encoded by pta.

Figure 14:
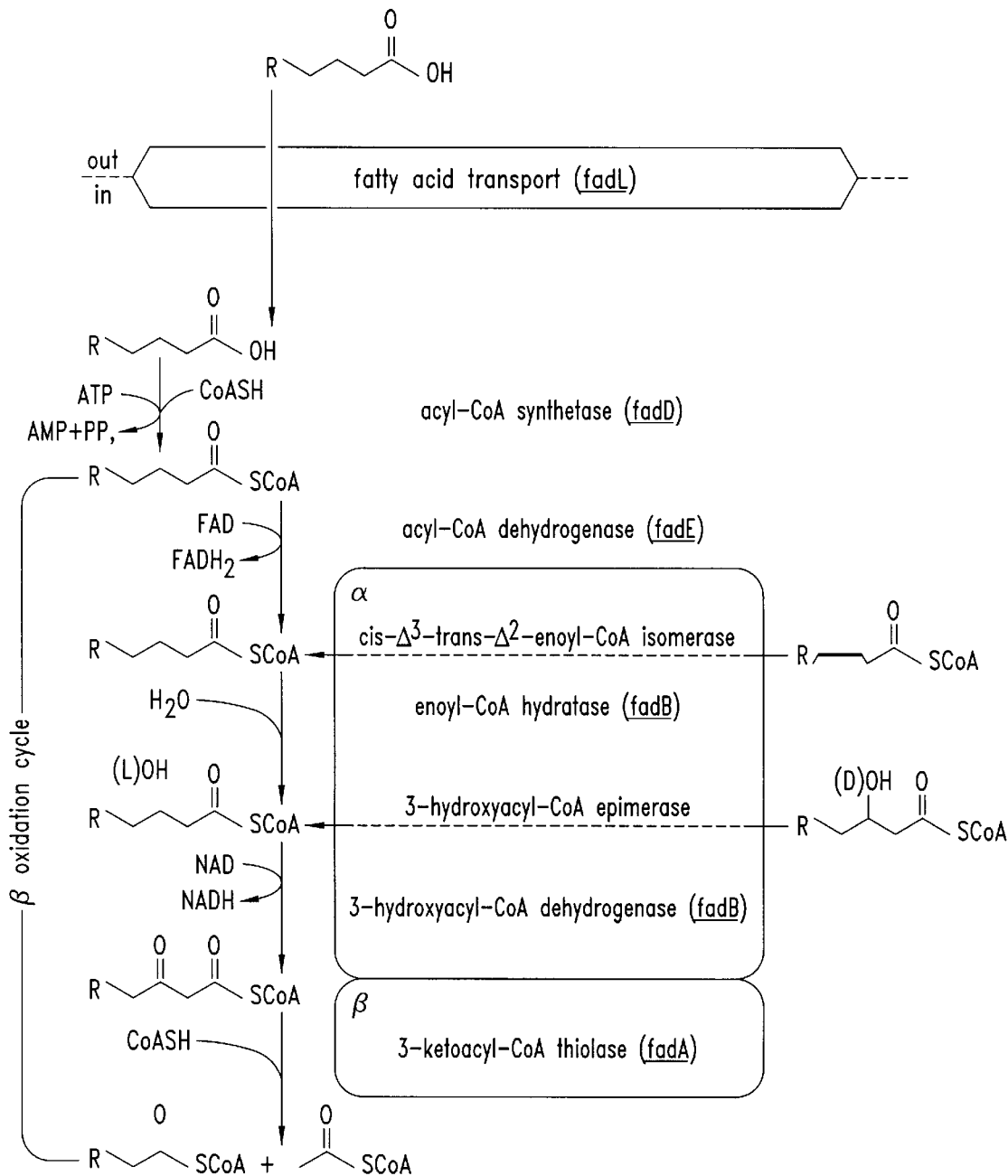
FIG. 14 is a schematic depiction of the fatty acid oxidation system.
Figure 15:
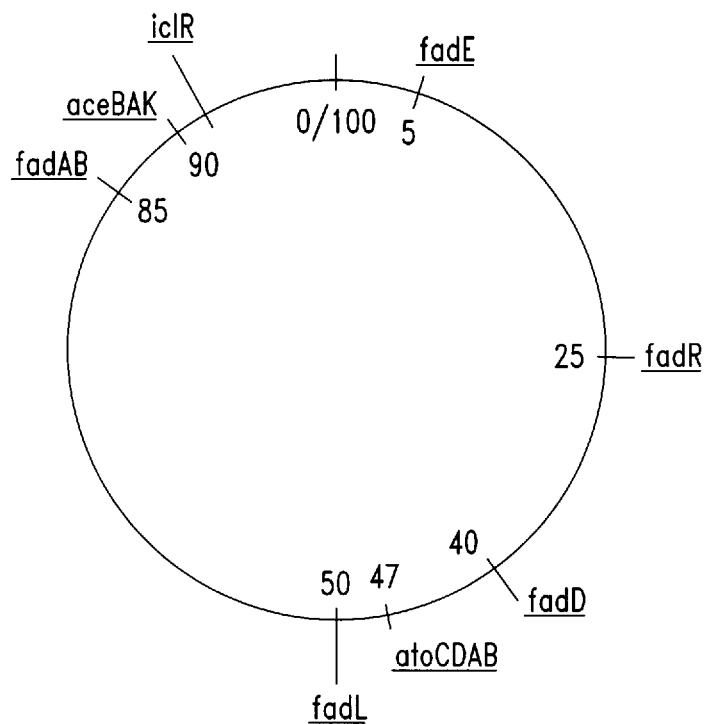
FIG. 15 is a map which depicts the location of the fad genes on the *E. coli* chromosome.

Briefly, the fadR gene ("fad" stands for fatty acid degradation) encodes a repressor that represses transcription of several different metabolic pathways in the *E. coli* cell, most notably, the fatty acid oxidation (FAO) system. The FAO system is responsible for the uptake and the breakdown of exogenous fatty acids (FIG. 14). Briefly, the fatty acid is transported through the cell membrane by the action of fadL, and is immediately activated to an acyl-CoA thioester by the action of acyl-CoA synthetase (encoded by fadD). This enzyme has broad substrate specificity and has been shown to act on both medium-chain fatty acids ("MCFA," C7–C11) and long-chain fatty acids ("LCFA," C12–C18). In the next step the acyl-CoA thioester is oxidized by the action of acyl-CoA dehydrogenase (fadE). Subsequently, a large multienzyme complex (encoded by fadB), having 5 different fatty acid oxidation activities processes the thioester so that it is a suitable substrate for the final enzyme of fatty acid oxidation, 3-ketoacyl-CoA thiolase. This enzyme breaks the beta bond, and removes an acetyl-CoA molecule. Under normal conditions, *E. coli* is able to grow on LCFA, but not MCFA. This is because LCFA are able to induce the expression of fatty acid oxidation enzymes, but MCFA cannot. However, in the case where there is a mutation in the fadR repressor, the FAO enzymes are constituitively expressed and the cell can grow on both MCFA and LCFA. The fad system is genetically well-characterized, with the genes being mapped at the following positions on the *E. coli* chromosome: fatdL—50 min, fadE—5 min, fadD—40 min, fadR—25 min, and fadAB—85 min (an operon) (see FIG. 15).

The atoC gene is part of an operon that encodes atoB, atoA, and atoD. The products of these genes are required for growth by *E. coli* on short chain fatty acids ("SCFA," C4–C6) as the sole carbon source, because it has been shown that while the fad system can utilize these fatty acids, their action alone is not sufficient to metabolize SCFA. It appears that the primary function of the ato system is in transporting SCFA into the cell (atoA and atoD) so that the fatty acids can be processed by the action of enzymes encoded by fadE, fadB, and atoB. The specific action of atoC is as a positive regulator, because in *E. coli* mutants in where the atoC gene product is expressed constituitively, the gene products of atoA, atoB, and atoD are also expressed, enabling an *E. coli* fadR strain to grow on SFCA as the sole carbon source (Pauli and Overath, *European Journal of Biochemistry* 29:553–562; 1972). The ato system has been mapped at 47 minutes on the *E. coli* chromosome and the organization of the operon has been elucidated.

Mutants at the fadR and atoC loci may be readily isolated essentially as described by Pauli and Overath (*European Journal of Biochemistry* 29:553–562; 1972). Briefly, since only fadR mutants are able to grow on MFCA as the sole carbon source, a log-phase *E. coli* culture may be plated at different dilutions on minimal medium plates containing decanoate as the sole carbon source. The only cells that will be able to grow are far spontaneous mutants (point mutations). In the same manner, these fadR clones may then be grown to log-phase, and plated onto minimal medium plates containing butanoate as the sole carbon source, selecting for spontaneous mutations in which the atoC gene is expressed constitutively, atoC (Con). This is the method by which *E. coli* LS5218fadR atoC was constructed.

As noted above, two other genes which encode proteins which regulate acetate/propionate metabolism are ack and pta. Briefly, conversion of acetate to acetyl-CoA may be accomplished by two different enzymatic systems. The first is the acetate kinase/phosphotransacetylase system found in *E. coli*. In this system the acetate kinase (ack) converts acetate to acetyl phosphate, which is then converted to acetyl-CoA by the action of phosphotransacetylase (pta). The ack gene may be readily obtained as described below in the Examples. The pta gene may be readily obtained following the methods described by Yamamoto-Otake et al. in *Applied Microbiology and Biotechnology* 33:680–682, 1990. The second method for conversion of acetate to acetyl-CoA is via an acetyl-CoA synthetase. Normally, acetyl-CoA synthetase enzymes are inducible (by their substrate, acetate), and have significant activity using propionate as the substrate (Jetten et al., *Journal of Bacteriology* 171:5430–5435; 1989). As shown in the Examples below, the ack gene and pta gene may be utilized in order to obtain high levels of 3-HV incorporation into a copolymer.

Figure 16:
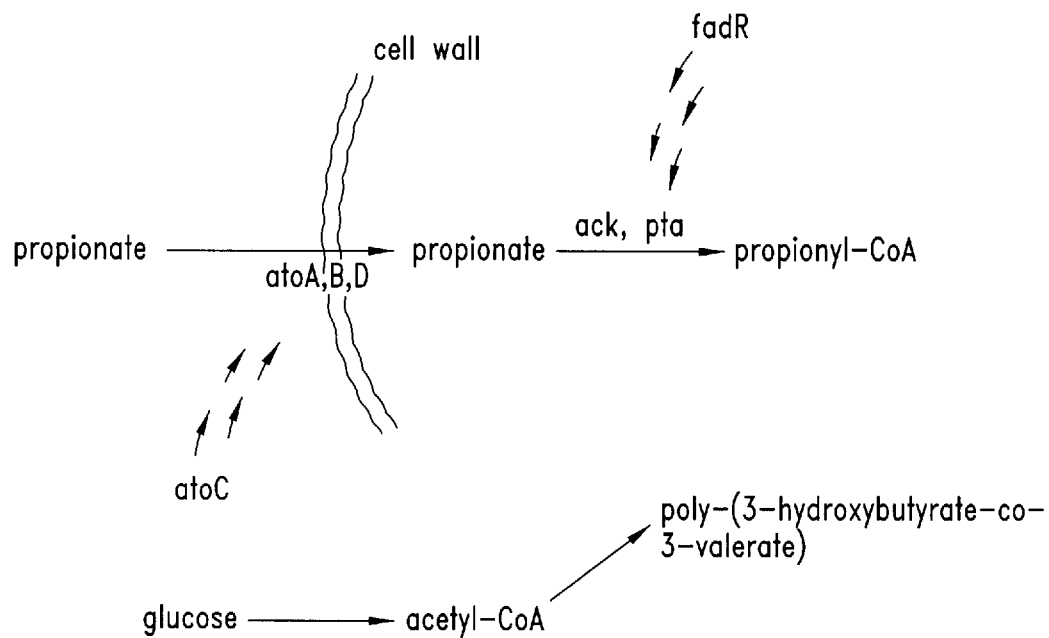
FIG. 16 is a diagrammatic representation of the interaction of the ato system, fad R, ack and pta.

Given the fact that both the fad and ato system are only shown to be functional in C4 to C12 fatty acid oxidation, prior to the present invention it was not clear that these genes could be involved in uptake and metabolism of propionate to propionyl-CoA. Nevertheless, during the course of experimentation a clear picture has emerged that both fadR and atoC are operational in copolymer synthesis. The salient results of these findings are diagrammed in FIG. 16. Briefly, the key facets are: 1) the ato system, controlled by atoC, is responsible for the uptake of propioniate, 2) once inside the cell, propionate is converted to propionyl-CoA primarily by the action of acetate kinase (ack gene) and phosphotransacetylase (pta gene), and 3) the fad system appears to raise the level of ack/pta activity slightly. Specific experiments that lead to these conclusions are set forth below in the Examples.

As noted above, PHA copolymer production may also be accomplished by introducing into a host cell a vector which co-expresses a sequence encoding a poly-beta-hydroxybutyrate biosynthetic pathway and one or more proteins which regulate acetate and propionale metabolism, or, by merely introducing a vector construct which directs the expression of one or more proteins which regulate acetate and propionate metabolism into a prokaryotic host cell which already produces poly-beta-hydroxybutyrate.

The host cell is then cultured in medium containing propionate or a derivative thereof. Briefly, as will be understood by one of ordinary skill in the art, a variety of propionates (wherein propionates are represented by -βC-αC-CO$_2$X; and X is either a cationic metal or alkyl group) may be utilized within the present invention. Examples include either monosubstituted or disubstituted propionates wherein the substituent groups may be selected from halogens (e.g., fluorine, chlorine, bromine, and iodine), oxygen (alcohols and their derivatives, including O—N, O—S, and O—P compounds), sulfur (thiols and their derivatives, including S—O compounds), and phosphorous (including phosphines, phosphites and phosphates).

Preferred conditions for culture of the host cell will vary with the host and the vector construct selected. For example, *E. coli* is normally grown at 37° C., in an orbital incubator (225 rpm). However, with some vectors, it may be grown at 30° C. to keep the vector uninduced, and at 34 to 38° C. to induce the vector. Preferably, the host cell is grown on minimal media (e.g., M9 minimal media), and is grown past the log phase and into the stationary phase of bacterial growth.

Once the host cell has been cultured under conditions and for a time sufficient to generate poly-β-hydroxyalkanoate copolymer, the poly-β-hydroxyalkanoate copolymer is isolated from the host cell. Isolation may be accomplished by a variety of methods. For example, the host cells may be lysed, and PHB agglomerated essentially as described in U.S. Ser. No. 07/528,549, which is hereby incorporated by reference in its entirety. Alternatively, lysozyme plasmids may be introduced into the host cell, and thereby utilized to enhance isolation of PHB. Such methods are described in detail in U.S. Ser. No. 07/890,925, filed May 29, 1991, which is hereby incorporated by reference in its entirety.

Within a preferred embodiment, after the host cells have reached the stationary phase of growth, they are washed once with water to remove debris. The cells are then heat sterilized, and while still hot, SDS (approximately 0.1%) and EDTA (approximately 2 mM) are added, and the mixture is stirred for about one hour at a temperature of 60° C. to 80° C. During this time, the cells will lyse, releasing the PHA granules. The granules are separated from cell debris by centrifugation, and then washed twice with water.

Through use of the above-described techniques, PHA may be isolated to approximately 98% or 99% purity, as determined by gas chromatography. Briefly, PHA purity may be calculated by determining the area under the PHA peak, and dividing it by the areas under all peaks in the chromatogram.

Experiments have been conducted which include the cloning of the PHB biosynthetic pathway and the production of PHAs in *E. coli* to a high internal concentration. All chemicals used in the experiments were reagent grade and were obtained from the Sigma Chemical Company of Missouri o from United States Biochemicals of Ohio. *A. eutrophus* H16 *E. coli* LE392, and *E. coli* DH1 were obtained from the American Type Culture Collection (ATCC) of Maryland. *E. coli* DH5 was obtained from the Bethesda Research Laboratories. Luria Broth (LB) and antibiotics were prepared according to the methods described in Maniatis et al., *Molecular Cloning: A Laboratory Manual*, Cold Spring Harbor Laboratory, New York, 1982. The cosmid PVK102 was obtained in *E. coli* HB101 from the ATCC. The methods, genes, and products of their expression and polymer synthesis are described in detail in the following non-limiting discussion.

Generation and Initial Screening of the *A. eutrophus* H16 Library

A cosmid library of *A. eutrophus* H16 total DNA was constructed by inserting 20-kb to 25-kb DNA fragments in PVK102, followed by transduction of *E. coli* LE392. Total *A. eutrophus* H16DNA was extracted by the sarcosyl lysis method described in Pritchard et al., *Basic cloning techniques; a manual of experimental procedures*, Blackwell Scientific Publications, London, 1985. A series of partial SalI restriction endonuclease digests of the DNA was conducted in order to determine the reaction conditions that would yield the maximum percentage of DNA fragments in the 20-kb to 25kb range. By using the parameters obtained from the calibrating reaction, a large scale digest was performed and the DNA was purified by phenol extraction and ethanol precipitation. The cosmid pVK102 was extracted according to the method of Hansen et al *J. Bacteriol.*, 135:227–238, 1978. The cosmid pVK102 was then purified in a cesium chloride (CsCl) gradient, digested with SalI, and purified by phenol extraction and ethanol precipitation. The partially digested genomic DNA fragments and the cosmid were mixed at an insert-to-vector molar ration of 20:1 at a final total NA concentration of 400 ug/ml, and the mixture as subjected to ligation overnight at 14° C. Part of the ligation was packaged by using the Promega Packagene kit, available from Promega Biotec of Wisconsin, and the packaged cosmids were used to transform *E. coli* LE392. The bacteria were plated onto plates of LB plus kanamycin, and resultant clones were picked for use in the library. Approximately 1,100 clones were picked for further assay. Of these clones, nine percent were polycosmids. Clones were stored individually in LB plus 15% glycerol at −85 C.

The cosmid library was initially screened by assaying for beta-ketothiolase activity. The enzyme assay for beta-ketothiolase (thiolysis reaction) was conducted using the method of Senior et al. *Biochem. J.*, 134:225–238, 1973. Cell extracts were prepared for enzyme assay according to the following procedures: one milliliter of an overnight culture in LB was pelleted by centrifugation in a microcentrifuge for one minute; the supernatant was removed, and the pellet was resuspended in 200 ul of breaking buffer which was comprised of 20 mM potassium phosphate buffer at Ph 7.2, 5 mM magnesium chloride ($MgCl_2$), 1 mM ethylenediaminetetraacetic acid (EDTA), 1 mM dithiothreitol, and 1M glycerol; the suspension was subjected to sonication using an Artek 300 sonicator with a microprobe at the maximum setting wherein sonication consisted of four fifteen second bursts; the sonic extract was subjected to centrifugation in microcentrifuge for five minutes; and the supernatant was transferred to a different microcentrifuge tube on ice for analysis. For assays done at later times, the cells were pelleted by centrifugation in a microcentrifuge at room temperature for one minute, the supernatant was removed and the pellets were stored at −85° C. until assay, at which time the pellets were resuspended and sonicated as described above.

In the beta-ketothiolase activity test, positive activity was measured in terms of micromoles of acetoacetyl-CoA degraded per minute per milligram of protein. Note that the reaction was assayed in the reverse direction but that one could also assay for acetoacetyl-CoA produced. To facilitate screening, 5 ml cultures of each cone were grown and then pooled in groups of five for assay. FIG. 2 shows that beta-ketothiolase activity was measurable in *A. eutrophus*, but not in *E. coli* LE392 lysates which had been cleared of particulate matter. Of the more than two hundred pools that were screened, six were positive for beta-ketothiolase activity. Individual clones from each pool were screened, and activity was traced to six clones which are identified in FIG. 2. The activities of the beta-ketothiolase-positive recombinants ranged between SO and 15% of that found in *A. eutrophus* H16 (FIG. 2 shows the results from a single run of a series of six runs and the 50% figure was determined from the series of six runs).

Screening of the beta-ketothiolase-positive recombinants.

The six recombinant clones which were positive for beta-ketothiolase activity were further screened by assaying for acetoacetyl-CoA reductase activity and by monitoring PHB accumulation. The enzyme assay for acetoacetyl-CoA reductase was conducted according to the methods covered in the Senior et al. article, supra. Acetoacetyl-CoA reductase activity was measured in terms of micromoles of NADPH oxidized per minute per milligram of protein. Protein was measured using the Bio-Rad R protein assay available from the Bio-Rad Laboratories of California. The PHB accumulation assay was done according to the method of Ward et al. *Anal. Biochem.,* 52:607–613, 1973, except that Whatman GF/A/F filters were used instead of Whatman GF/A filters. PHB amounts were calculated from a standard curve by using known quantities of DL-hydroxybutyrate.

FIG. 2 shows that three recombinant clones, which harbor cosmids pAE65, pAE175 and pAE689, respectively, were positive for acetoacetyl-CoA reductase activity and PHB production. The clone harboring pAE65 expressed acetoacetyl-CoA reductase activity to a much higher level than did *A. eutrophus* H16 but produced a very small amount of PHB. Conversely, acetoacetyl-CoA reductase activity in clones harboring pAE175 and pAE689 was extremely low when compared to that of *A. eutrophus* H16, but both clones produced PHB to approximately 50% of the concentration achieved in *A. eutrophus* H16. IT is believed that the low reductase activity and high PHB production exhibited by clones harboring pAE175 and pAE689 is the norm and that pAE65 reductase activity is an artifact which results from scrambling of the DNA fragments in the cloning process. The fact that restriction digest patterns of pAE65 was quite different provides support for this belief. Subcloning of pAE175 fragments.

Figure 3:
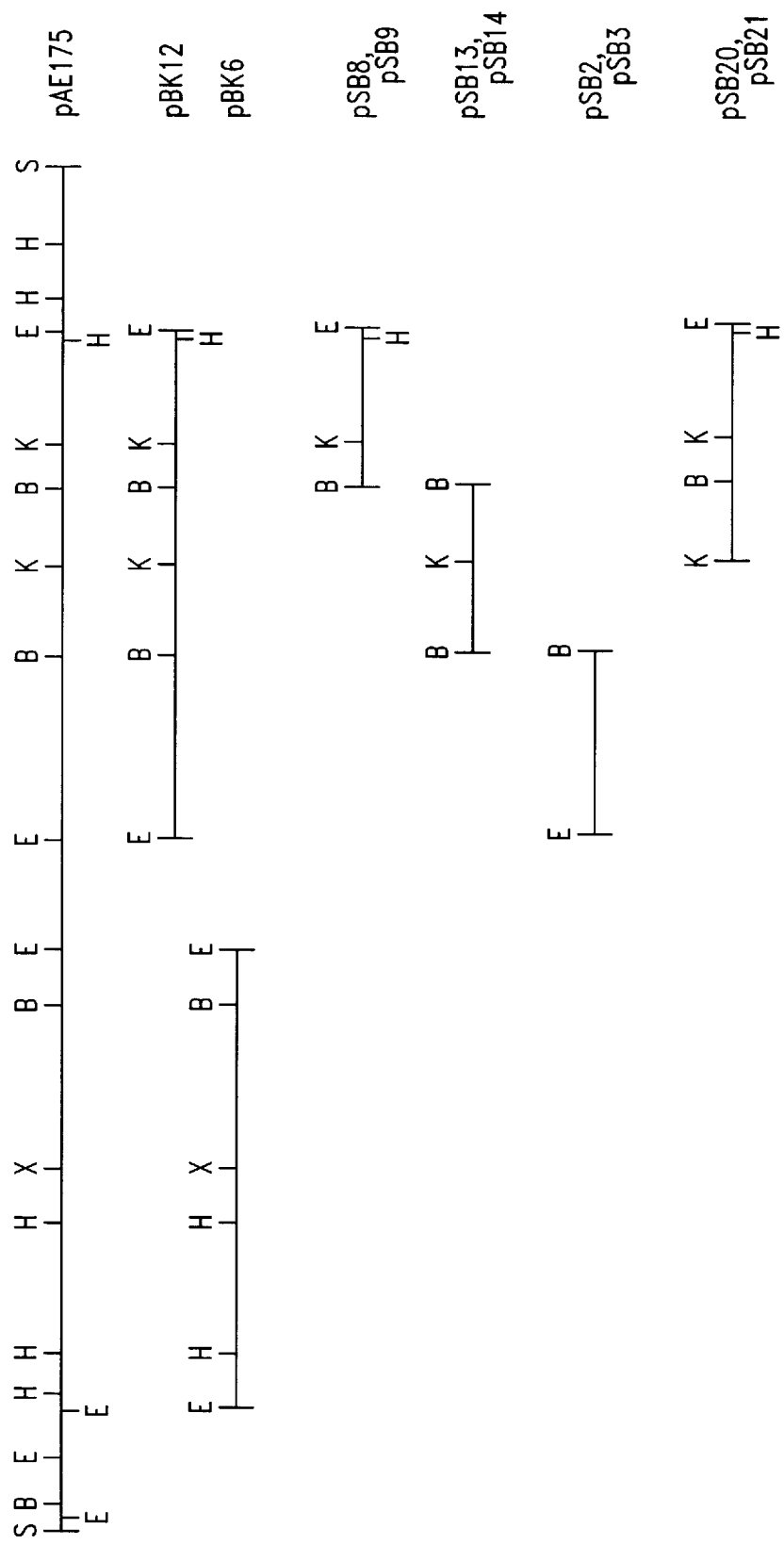
FIG. 3 is a restriction endonuclease map of the cosmid pAE175 insert showing subcloned restriction fragments; abbreviations of restriction endonucleases are as follows: B, BglII; E, EcoRI; H, BamHI; K, KpnI; X, XhoI; S, SalI.

FIG. 3 shows a restriction endonuclease map of the pAE175 cosmid DNA insert. Two central EcoRI fragments were subcloned into the plasmid pUC13, a plasmid available from Pharmacia. Subcloning of the cosmid and plasmid DNA fragments was performed according to the following procedures: recombinant cosmids were purified according to method of Hansen et al., supra; the purified recombinant cosmid was digested with the appropriate restriction endonuclease; and the fragments to be cloned were isolated in low melting temperature agarose as described in Burns, *Anal. Biochem.,* 135:48–51, 1983. Ligation reactions contained plasmids and insert DNA at a 1:3 ratio, respectively. Restriction enzymes and T4 DNA ligase were purchased from Bethesda Research Laboratories of Maryland or from United States Biochemicals. Seakem GT agarose, available from the FMC Corp., Marine Colloids Division, of Maine, was used as the agarose.

Two clones, harboring pBK12 and pBK6 EcoRI restriction fragments, respectively, were picked and analyzed for betaketothiolase activity, acetoacetyl-CoA reductase activity, and PHB production. FIG. 4 shows an analysis of subclones for enzyme activity and PHB production where interestingly, high betaketothiolase activity was detected in both clones. However, acetoacetyl-CoA reductase activity and PHB production was only detected in clones harboring pBK 12. The pBK 12 insert is approximately 14 kb in length. As in clones harboring pAE175 and pAE689, the acetoacetyl-CoA reductase activity in the clone harboring pBK12 harboring clone was lower than that found in the PHB producing cosmid clones.

It is known that the PHB pathway has a biosynthetic portion and a degradative portion and is made up of five enzymes. In Dawes et al., *Adv. hMicrob. Physiol.,* 14:135–266, 1973, it is pointed out that beta-ketothiolase is both the entry and exit point of the cycle. The existence of two beta-ketothiolase activities raises the possibility that the activity found on pBK12 is part of the biosynthetic portion while the activity found on pBK6 is part of the catabolic portion. To test the possibility that pBK6 contained part or all of the biodegradative pathway, the clone was assayed for two of the remaining three catabolic enzymes, D-3 hydroxybutyrate and succinyl-Co-A transferase. The enzyme assays were performed according to the methods of Senior et al., supra. Neither activity was found in lysates of *E. coli* harboring pBK6, *E. coli* harboring pBK12, or *E. coli* harboring pAE175, whereas both activities were easily measured in *A. eutrophus* H16. Therefore, the betaketothiolase activity on pBK6 is unexplained; however, there is a possibility that the three remaining catabolic enzymes are simply not proximal to the beta-ketothiolase gene.

Plasmid pBK12 was further subcloned by digesting it with EcoRI and BglII. Two EcoRI-BglII fragments and one BglII fragment were obtained and each fragment was approximately 4 kb in length. Six subclones, representing each portion of the pBK12 insert in duplicate, were picked and assayed for beta-ketothiolase activity, acetoacetyl-CoA reductase activity, and the PHB accumulation, as described above. FIG. 4 shows beta-ketothiolase activity and acetoacetyl-CoA reductase activity were detected in *E. coli* harboring plasmids pSB8 and pSB9. FIG. 3 shows the *E. coli* harboring plasmids pSB8 and pSB9 as the right most BglII-EcoRI fragment. The activities expressed in pSB8 and pSB9, shown in FIG. 4, are considerably higher than those expressed in *A. eutrophus.*

The data from analyses of pSB8 and pSB9 were interpreted to mean that the first two enzymes of the PHB biosynthetic pathway are located on the 3,500 base BglII-EcoRI fragment, but that the third enzyme, PHB synthetase, was either cleaved by BglII or is positioned to the left of the BglII site. To obtain the whole pathway on a sequence small enough to use in DNA sequence studies, a 5.5 kb Kpnl-EcoRI fragment was cloned into pUC18, a plasmid obtained from Bethesda Research Laboratories of Maryland. Two clones harboring pSB20 and pSB21 were tested and both clones exhibited beta-ketothiolase activity, acetoacetyl-CoA reductase activity and PHB production. FIG. 4 shows the subclones pSB20 and pSB21 accumulated nearly as much or more PHB as *A. eutrophus*H16. FIG. 3 shows a restriction endonuclease map of the pSB20 and pSB21 fragments relative to the pAE175 cosmid insert. Comparison of *A. eutrophus* H16 DNA with cloned DNA.

Figure 5:
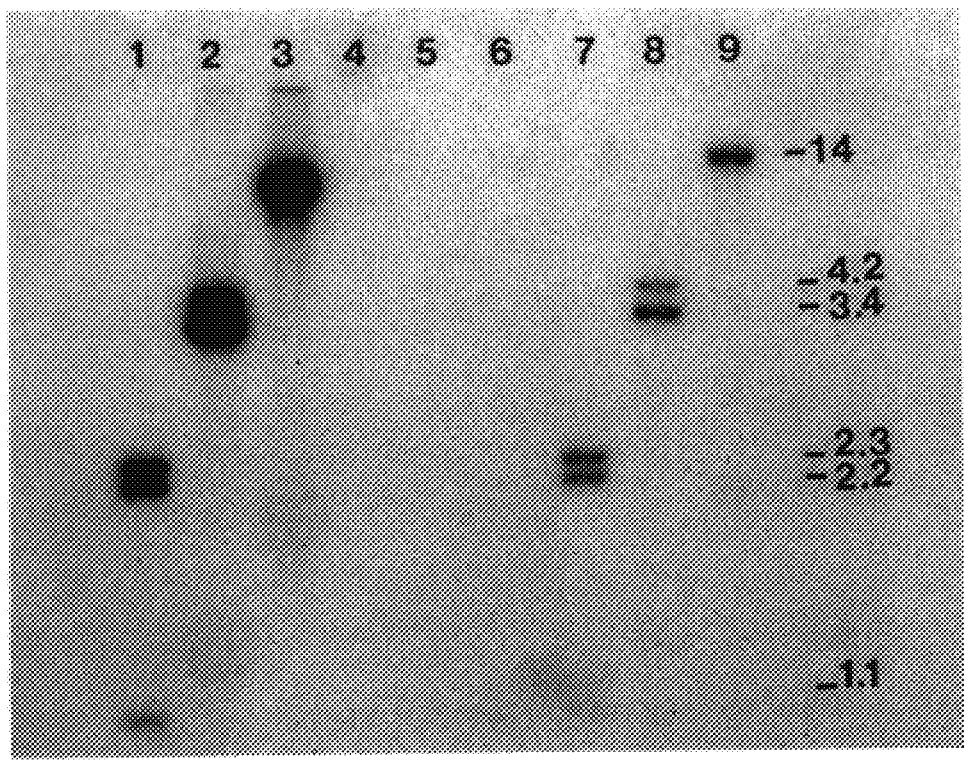
FIG. 5 is a Southern blot analysis of DNA from *E. coli* harboring PAE175 (lanes 1 to 3), *E. coli* LE392 (lanes 4 to 6) and *A. eutrophus* H15 genomic DNA (lanes 7–9); lanes 1, 4 and 7, EcoRI; lanes 2, 5 and 8, EcoRI-BglII; lanes 3, 6 and 9, SalI.

Because the manner in which the PHB pathway was cloned left open the possibility that the cloned fragment was a product of scrambling, Southern blot analysis was performed to demonstrate that the PHB biosynthetic pathway in *A. eutrophus* H16 was the same restriction pattern as that of the cloned PHB DNA. Southern blot analysis was performed by the method of Maniatis et al., supra. The probe was made radioactive by using a random primer extension kit obtained from DuPont, NEN Research Products, of Massachusetts. Digested pAE175 was compared to digests of DNA extracted from *A. eutrophus* H16 and *E. coli* LE392. Restriction endonucleases used were EcoRI, EcoRl-BglII, and SalI, respectively. A gel purified 5.2 kb PHB fragment was labeled and used as a probe. FIG. 5 reveals that the PHB biosynthetic pathway is located on a 14 kb EcoRI fragment in *A. eutrophus* H16 (shown in lane 7) and in pAE175 (shown in lane 1). No hybridization could be detected to any DNA fragments to *E. coli* LE392 (lanes 4 through 6). Further digests of pAE175 and *A. eutrophus* genomic DNA manifested the same restriction patterns, indicating that the cloned PHB biosynthetic pathway was the same as that found in *A. eutrophus* H16.

PHB in *E. coli*

Figure 6A:
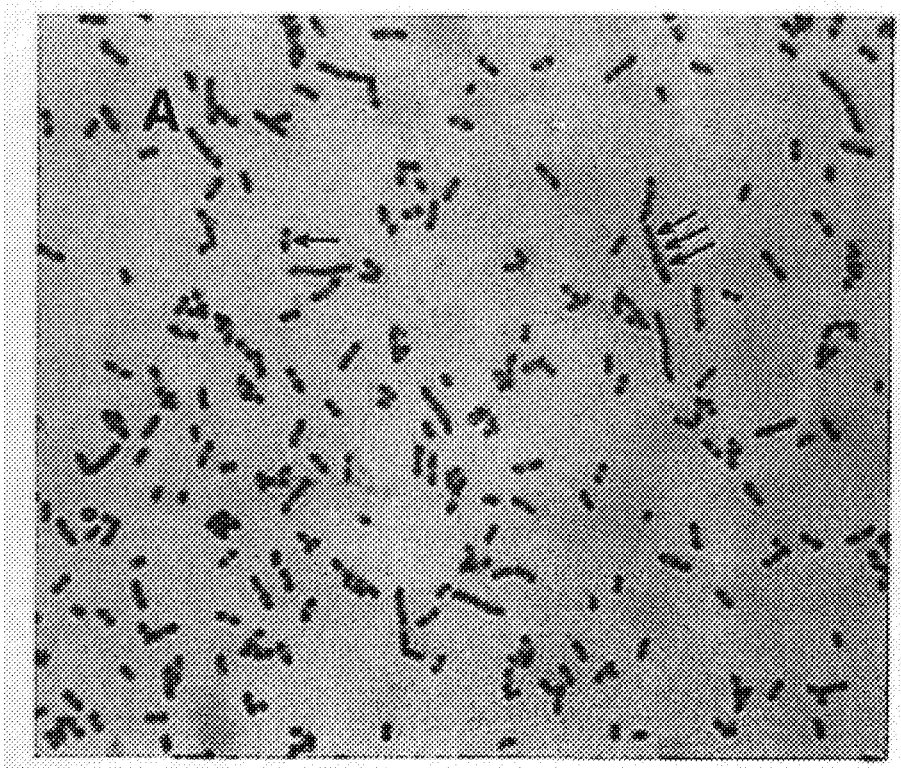
FIGS. 6a and 6b are photomicrographs of *A. eutrophus* H16 and *E. coli* harboring PSB20, respectively, showing intracellular PHB granules (arrows); magnification, ca. 3,000.
Figure 6B:
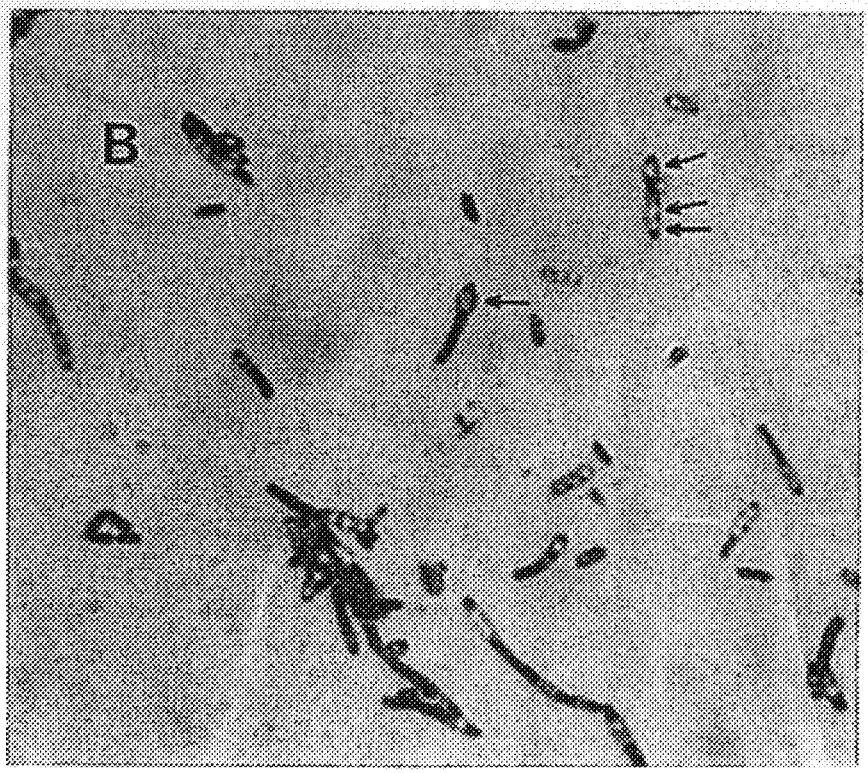

FIGS. 6*a* and 6*b* show that PHB is produced in granules in both *A. eutrophus* H16 and *E. coli* harboring the pSB20 plasmid insert Twenty four hour cultures of *A. eutrophus* H16 and *E. coli* harboring pSB20 were stained for fifteen seconds with crystal violet. The crystal violet is absorbed by the cells, but PHB granules are refractile to the stain. The cultures were examined under an oil immersion lens. FIG.

6a shows PHB granules in *A. eutrophus* are evident as fuzzy, non-staining areas between stained regions of the bacterium. FIG. 6b shows PHB granules in *E. coli* much more distinctly. Granule formation in *E. coli* appears to differ from that in *A. eutrophus* H16 in that the granules in *E. coli* were more numerous and were often larger in diameter than the cell. PHB granules in *A. eutrophus* H16 did not usually distend the cell membrane.

Figure 7:
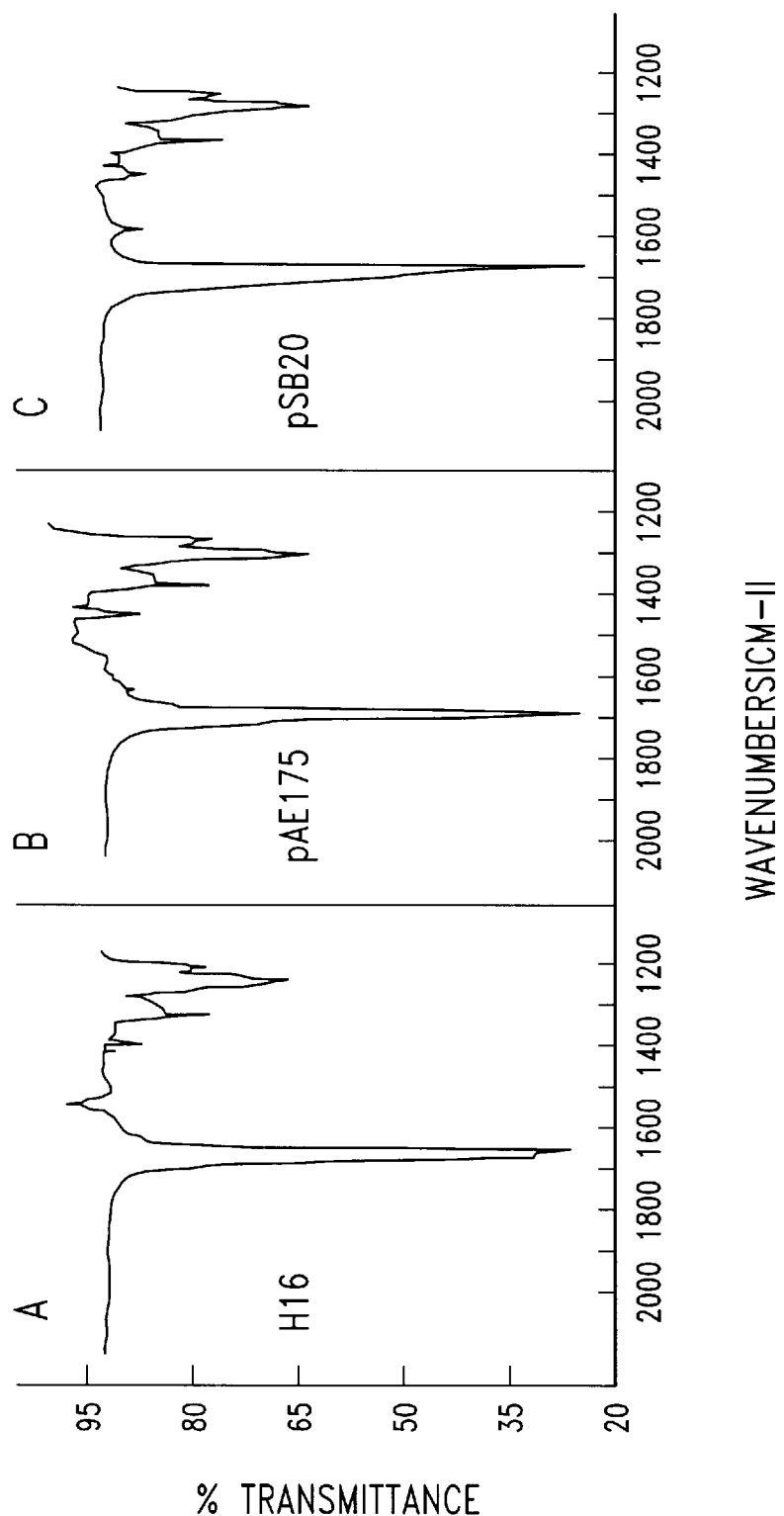
FIG. 7 is a graph showing infrared (IR) spectra of PHB extracted from *A. eutrophus* (A), *E. coli* harboring PAE175 (B), and *E. coli* harboring PSB20 (C).

FIG. 7 shows IR spectra of PHB which was extracted from *A. eutrophus* (A), *E. coli* harboring pAE175 (B), and *E. coli* harboring pSB20 (C). The infrared (IR) spectra of various PHB samples was obtained utilizing the technique described in Wakisaka, *Appln. Environ. Microbiol.*, 43:1473–1480, 1982. The results demonstrate that the PHB produced in its native state (i.e., *E. coli* harboring pAE175 and *E. coli* harboring pSB20) have virtually identical IR spectra In addition, the PHB spectra shown in FIG. 7 are very similar to those from other organisms as indicated in Fernandez-Casillo et al., *Appln Environ. Microbiol.*, 51:214–216, 1986, and in Senior et al., supra.

Production of PHB

Experimental results showed that *E. coli* harboring both pAE175 and pAE689 cosmid clones produced PHB to approximately 50% of the level achieved in *A. eutrophus* H 16. Substantial levels of intracellular PHB were accumulated in *E. coli*. These levels approached 90% of the bacterial cell dry weight in some subclones, and PHB was observable as large intracellular bodies. The high levels of expression obtained implies either a high degree of transcriptional versatility or a high degree of transcriptional homology.

PHB was grown in *E. coli* harboring the PHB biosynthetic genes under conducive conditions, i.e., a flask of LB is inoculated with the *E. coli* harboring the PHB biosynthetic pathway and the *E. coli* are grown in the presence of 1% glucose (where glucose acts as the carbon source for PHB production).

A strain of *E. coli* harboring the PHB biosynthetic pathway which was produced according to the techniques described above has been deposited with the American Type Culture Collection of 12301 Parklawn Drive, Rockville, Md. on Jun. 5, 1989 and bears deposit number: 68006. The strain (pGEM-PHB) is like that of pSB20 where the PHB biosynthetic pathway was isolated on a DNA fragment approximately 5.5 kb in length. The advantage of the smaller vector over the larger cosmid clone pAE175 is the ability to produce more copies. Access to the microorganism shall be made available to the public. p4A subclone.

A strain of *E. coli*, i.e., *E. coli* HMS174, was transformed by a vector containing the p4A plasmid with the PHB biosynthetic pathway and approximately four hundred extra bases on both the upstream and downstream sides of the pathway. The HMS 174 strain of *E. coli* was chosen because it contains a lactose utilization system and is recombination deficient so that a plasmid containing lactose genetic regions will not recombine and make the construct unstable.

Figure 9:
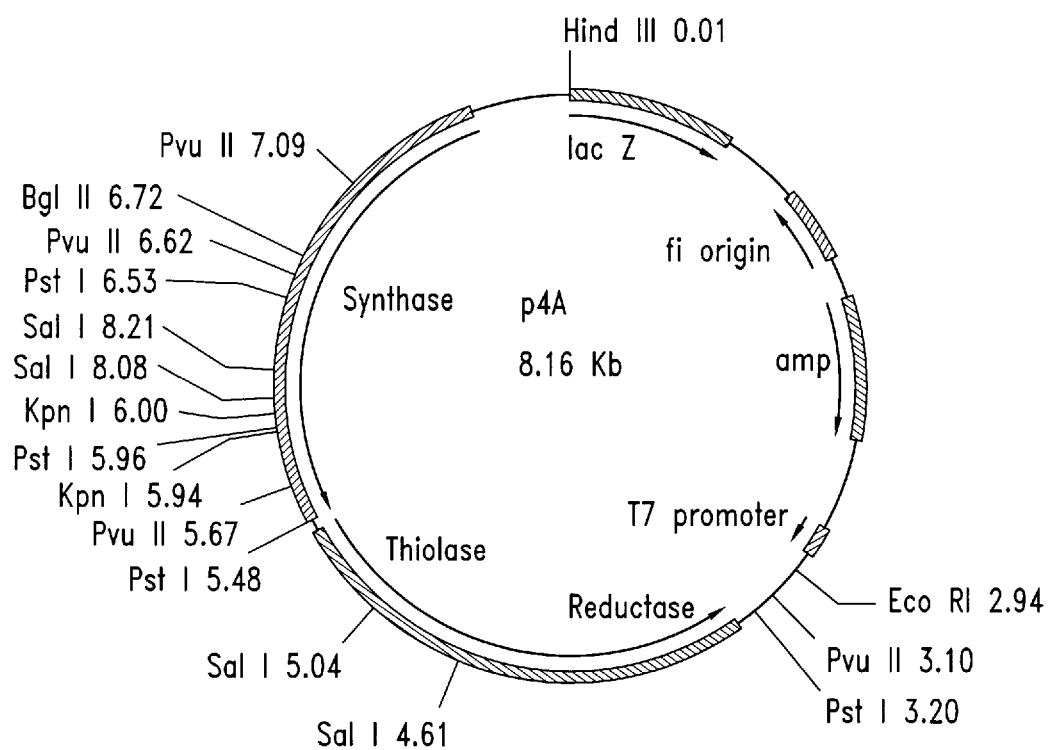
FIG. 9 is a diagram of the plasmid p4A.
Figure 10:
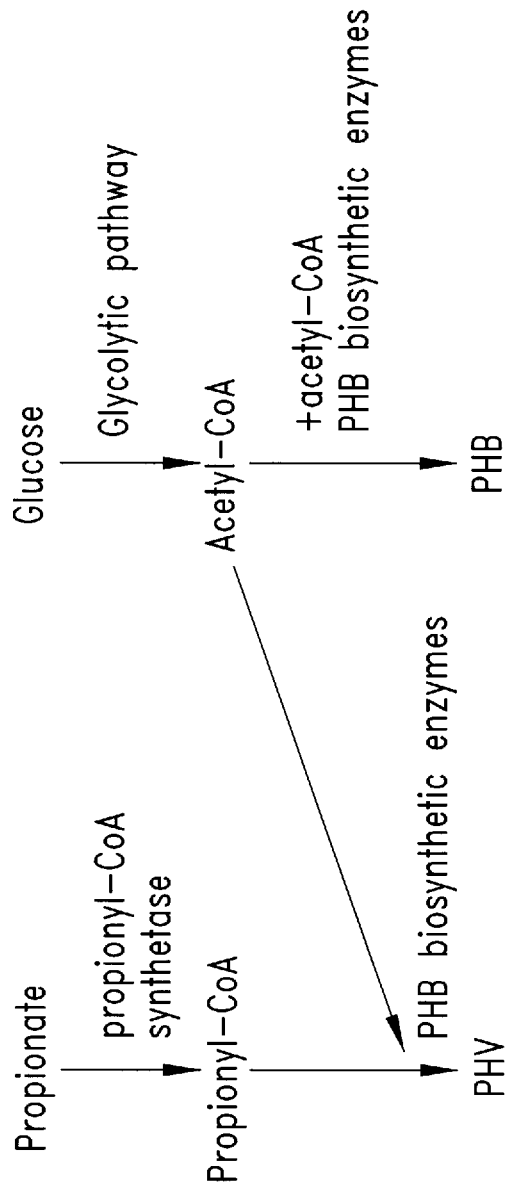
FIG. 10 is a schematic diagram of a pathway of PHB-coV production.

The *E. coli* strain HMS174 containing the plasmid p4A accumulates a greater percentage of PHB in a shorter period of time than other *E. coli* clones containing different plasmid constructs. The *E. coli* strain HMS174 is available from the Yale *E. coli* Stock Center, Barbara Bachman, curator. Clone (plasmid) p4A which contains the DNA for the poly-beta-hydroxybutyrate biosynthetic pathway was deposited in an *E. coli* HMS174 host in the permanent collection of the American Type Culture Collection, 12301 Parklawn Drive, Rockville, Md., on May 23, 1990. The culture was assigned the accession number ATCC: 68329 by the repository. Recombinant plasmid p4A can be isolated from its *E. coli* HMS 174 host by well known procedures, e.g., using alkaline lysis procedures, and the like. The p4A clone is shown in FIG. 9 and is described in the copending application Ser. No. 07/528,549, filed May 25, 1990 and Ser. No. 07/705,806, filed May 24, 1991, and published in Janes et al., E. A. Dawes (ed.) Novel Biodegradable Microbiol. Polymers 175–190, 1990, Kluwer Academic Publishers (printed in The Netherlands), all of which are expressly incorporated herein by reference.

The p4A plasmid exists in the cell ate an abnormally high copy number (50–200 per cell) thereby increasing the gene dosage of the PHB biosynthetic genes resulting in extremely high PHB production (as high as 95% of the cell weight). Thus, p4A is a "multicopy plasmid." The term "multicopy plasmid" is used in the sense of the ordinary definition and means a plasmid which exists in a plural number in a host cell.

The p4A construct has been placed in several different host strains, including *E. coli* strains, for example, DH1, DH5, BW313, HMS174, and CJ236. In all instances PHB was made to levels reaching 70–95% PHB wt/cell wt. It is to be noted that various other bacterial strains including, for example, Salmonella or other euteric organisms can also be used as the host strains.

The plasmid p4A is superior to other plasmids based on its copy number, because in alkaline minipreps the plasmid yield from p4A is about twice as much as other PHB-plasmids. Gene dosage effect may be responsible for high levels of PHB production in *E. coli*. To test this hypothesis, the PHB pathway was cloned into plasmid pOU71 obtained from Dr. Soren Molin (Larsen et al., *Gene* 28:45, 1984). This plasmid is maintained as a single copy when grown at 30° C. In experiments where the plasmid was maintained as a single copy, PHB production was $\frac{1}{40}$th of that found in 04A in *E. coli* DH5alpha If the PHB genes are found in single copies in *A. eutrophus*, this indicates that the genes are not well-expressed in *E. coli*, but overcome this deficit by having a large number of genes. This is supported by reports that, in general, *A. eutrophus* genes are not well-expressed in *E. coli*, but overcome this deficit by having a large number of genes. This is supported by reports that, in general, *A. eutrophus* genes are poorly expressed in *E. coli* (Anderson et al., *J. Bact.* 159:97, 1984).

PHA in *E. coli*

Figure 8:
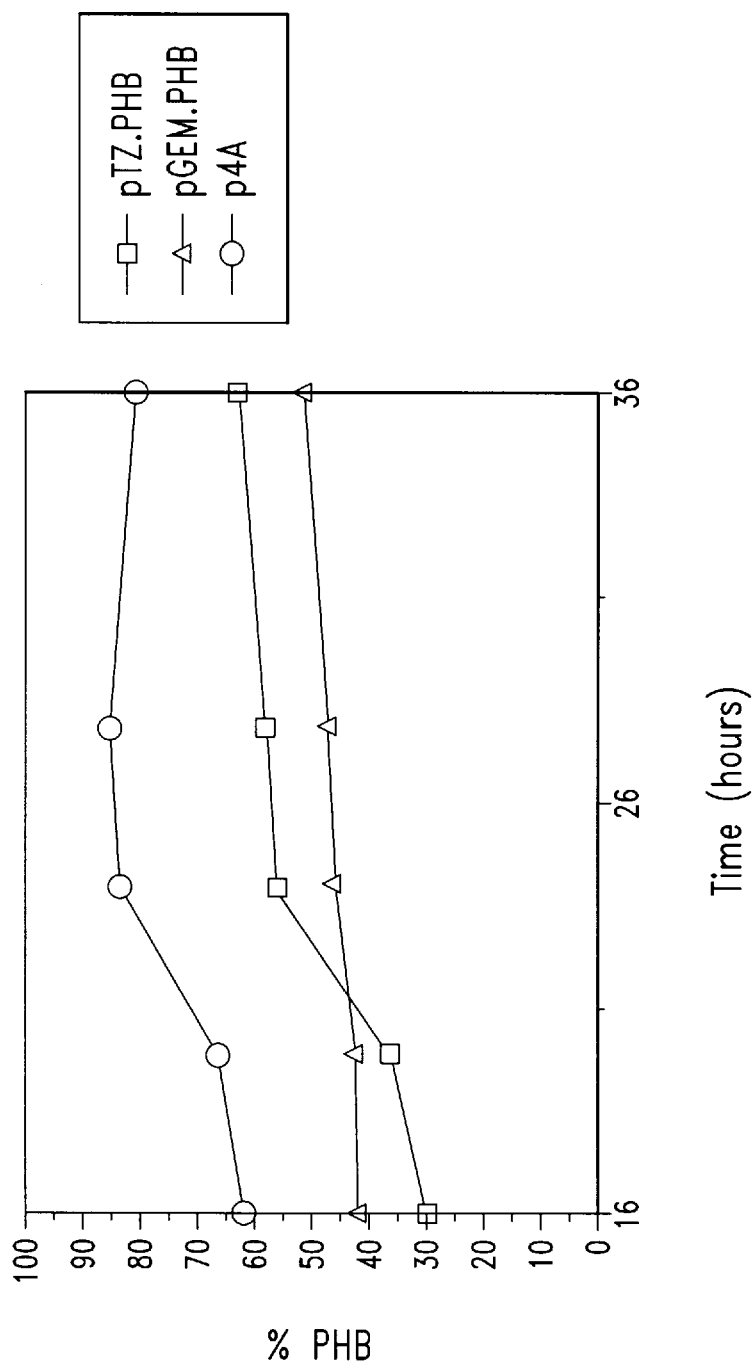
FIG. 8 is a line graph showing PHB accumulation versus time for a variety of clones containing different plasmid constructs.

Acetyl-CoA synthetase is able to utilize propionate as a substrate and change it to propionyl-CoA- Propionyl-CoA is then incorporated directly into PHB-co-V staring with the PHB biosynthetic enzyme beta-ketothiolase. The first enzyme of the PHB pathway, beta-ketothiolase, has a substrate specificity that allows it to act on propionyl-CoA as well as acetyl-CoA (Haywood et al., *FEMS Microbiol. Letters* 52:91, 1988). It has been proposed that acetyl-CoA synthetase accepts propionate as well as it's normal substrate, acetate (Campagnari et al., *J. Biol. Chem.* 238:1628, 1963; Hele, *J. Biol. Chem.* 206:671, 1952). Thus, the pathway of PHB-co-V production, as shown in FIG. 8, is believed to be as follows: propionyl-CoA and acetyl-CoA are condensed to acetopropionyl-CoA, which is then reduced to beta-hydroxyvaleryl CoA, which is subsequently polymerized into the PHB/PHV copolymer.

The enzymes needed for PHB-co-V production are not normally to be found in most host strains, including *E. coli*. However, acetyl-CoA synthetase is an inducible enzyme of the acetate utilization system in many host strains, including for example, Escherichia and Salmonella. According to the method of the present invention PHA production in the host is accomplished by inducing acetate utilization genes in a host and thereafter producing the PHAs by allowing the host cells containing the acetate utilization genes grow.

In one embodiment of the invention, a vector containing the DNA sequence coding for the poly-beta-hydroxybutyrate biosynthetic pathway is introduced into the host cell. The enzymes of acetate utilization are induced by growing the host cells on a first substrate. The first substrate comprises at lease one of the following: acetate, propionate, or combination of acetate and propionate, or other 3-carbon substrates. In a preferred embodiment the host cells are allowed to grow in the first substrate until the culture reaches late log phase. Thereafter, the host cells are cultured on a second substrate comprising a carbon source such as glucose, fructose, sucrose, lactose, maltose and the like. Alternatively, the host cell can be cultured in the first substrate prior to introducing the vector. The enzymes of acetate utilization, now present in the host cells, act on the propionate and incorporate the propionate into the PHA copolymers being produced by the host cells. The ratios between the various PHAs can be varied by altering the ratio between the first substrates. For example, acetate:propionate ratios can vary between 20–40:10–25 to produce concentration of PHV as high was about 50%, by weight, of the PHAs produced.

In another embodiment, the host can be a mutant in which the genes for acetate utilization are expressed constituitively. That is, they are present at all times. The p4A plasmid described above was cloned into E. coli cells which produced acetyl-CoA synthetase. The transformed E. coli cells were then grown on a substrate which comprises propionate and a carbon source. It is noted that various other carbon sources such as sucrose, fructose, lactose, maltose and the like are also useful as carbon sources in the present invention. These clones are able to incorporate propionate to form a copolymer comprising PHB and PHV.

The acetyl-CoA synthetase must be present in order to obtain PHV synthesis. Thus, in another embodiment, the acetyl-CoA synthetase gene can be cloned onto a plasmid and expression of the acetyl-CoA synthetase gene can be obtained from the plasmid. These clones can be used in a number of ways to regulate PHV synthesis; for example, PHV synthesis only occurs when the cloned acetyl-CoA synthetase gene is turned on.

The PHB/V currently produced is a random copolymer in that the valerate and butyrate are dispersed randomly in the polymer backbone. However, by controlling (by activating or suppressing) the acetate utilization gene it is now possible to generate "blocked" or semi-random copolymers. By alternately turning on and turning off the acetate utilization genes for a period of time (using, for example, chemical or heat induction) semi-random polymers are generated. The semi-random polymers comprise chains of butyrate molecules interspersed with chains of randomly dispersed molecules of butyrate and valerate. In addition, as described above, by controlling or varying the substrate, the composition of the PHAs generated are also varied.

The clones used in the present invention, which grown on the various substrates produce a copolymer of PHB/V to levels reaching 80–85% of the total cell weight. By varying the amount of propionate, it is possible to alter the ratio of PHB to PHV production by the host cell. PHV production up to and including about 50% by weight of the total cell weight, can be achieved using the present invention.

The following examples are offered by way of illustration, and not by way of limitation.

EXAMPLE 1

Genes which encode proteins that are involved in acetate and proprionate metabolism were induced in various E. coli strains, and then grown on acetate/propionate substrates, with and without glucose. The three E. coli strains utilized were obtained from Barbara Bachman of the E. coli Genetic Repository at Yale University. Two of the strains, E. coli LS5219 and E. coli LS5221, cannot utilize proprionate, whereas the third strain, E. coli LS5218, does utilize proprionate. As described in greater detail below, these strains of E. coli (LS5218, LS5219 and LS5221) were grown overnight, and then electroporated with p4A (also designated pJM8801; ATCC Deposit No. 68329).

A. Electroporation

Electroporation was accomplished essentially as follows. Briefly, a 3 ml tube culture of Luria Broth ("LB") was inoculated with the bacterial strain, and grown overnight on an orbital incubator (225 rpm) at 37° C. The next morning, 1 ml of the saturated culture was inoculated in 50 ml of M9, minimal medium containing 40 mM acetate and 10 mM proprionate, in a baffled 250 ml flask, and the culture was grown as above until the optical density at 600 nm reached approximately 0.7. At this time, the culture was placed on ice for 10 minutes. It was then transferred into a sterile 50 ml capped, conical-ended, plastic tube (Baxter Scientific), and centrifuged at 2,000 g for 10 minutes. The supernatant was aseptically removed and 40 ml of sterile ice-cold deionized water was added to the pellet. The pellet was resuspended by vortexing, followed by pelleting as described above. The supernatant was again aseptically aspirated, after which the pellet was again resuspended with 40 ml of sterile ice-cold, deionized water. The bacteria were again pelleted by centrifugation, and the supernatant was aseptically aspirated. Forty ml of sterile ice-cold water was added a final time, the pellet was resuspended, and a final pellet was obtained by centrifugation as above. The supernatant was again aseptically aspirated and the pellet was resuspended in a final volume of approximately 0.2 ml. One hundred microliters of this suspension was removed to a chilled microcentrifuge tube, and 1 μof plasmid DNA (p4A) was added and mixed This mixture was added to an electroporation cuvette (BioRad Laboratories), and subjected to a pulse of 2.5 kV at 200 mOhms, and 25 μfarads (Gene Pulser Apparatus, BioRad Laboratories). The cuvette was removed and the bacterial suspension transferred to a 3 ml culture of the M9 medium described above in a sterile 16×100 mm tube.

Ampicillin was added to a final concentration of 200 μg/ml, and then 1 ml of culture was inoculated into each of two flasks containing M9 Minimal Medium, 40 mM acetate and 10 mM propionate; to one of these flasks 0.4% glucose was added. The result was two cultures: one with glucose, and one without, both with acetate and propionate. The cultures were then allowed to grow. It was noted that the E. coli LS5221 (p4A) grew the fastest After 4 days growth, the optical density O.D. (600) was measured (see Table 1 below).

TABLE 1

|  | Ac/Prop | Ac/Prop/Gluc |
|---|---|---|
| E. coli LS5218 (p4A) | 0.1 | 4.78 |
| E. coli LS5219 (p4A) | 1.4 | 3.34 |
| E. coli LS5221 (p4A) | 1 | 4.74 |

Production of PHA was also determined by methanolysis and gas chromatography ("GC") analysis as described below.

B. Methanolysis

Duplicate 3 ml samples were taken from each flask and pelleted by centrifugation for 10 minutes at 2500 rpm in a Varifuge™ (Heraeus Instruments). Supernatant was aspirated and discarded, and the pellets frozen (−80° C. for 10 minutes). Tubes containing the frozen pellets were then placed in a Labconco™ lyophilizer for 20 minutes, or until samples were freeze-dried.

1.7 ml of ACS grade methanol (Mallinckrodt), 2 ml ACS grade chloroform (Mallinckrodt), 0.3 ml concentrated sulfuric acid (added while vortexing tube), and 0.1 ml benzoic acid solution (2 mg/ml) was added to each of the tubes. Samples were capped tightly, placed in a heat-block adjusted to 100° C., and incubated for 140 minutes. Samples were then removed from the heat-block and allowed to cool to room temperature. One milliliter of deionized water was then added to each tube, and the tubes were vortexed for 30 seconds, followed by centrifugation for 10 minutes at 2500 rpm. The upper aqueous phase and protein interface of each sample was aspirated off, and the remaining organic phase was pipetted into vials and assayed for PHB production by gas chromatography.

C. Gas Chromatography

A Shimadzu GC-14A connected to a CR-4A data processing unit, an AOC-14 autoinjector and an AOC-1400 autosampler were utilized for gas chromatography. The carrier gas was helium and detection was through a flame ionization detector. Flow rate of the carrier was approximately 5 ml/min. The column used for detection was a Supelcowax 10 column from Supelco Separation Technologies. The column was a 15 meter column, 0.53 mm inner diameter, with a 1 μm thick coating.

Samples (1 to 3 μl) were injected into the injection port (temperature 200° C.) and carried into the column. The samples were run under a temperature profile of 55° C. for 5 minutes, followed by a temperature ramp of 5° C. per minute until the column temperature reached 220° C. The temperature was held at 220° C. for 5 minutes, followed by termination of the run and cool-down for the next run. Typically, the solvent peak eluted through the detector (240° C.) between 1 and 2 minutes, and the PHB peak eluted between 3 and 4 minutes. Analyses were performed utilizing benzoic acid (100 μl of 2 mg/ml solution in methanolysis tubes) as an internal standard. Typically, benzoic acid eluted from the GC column approximately 5 minutes into the run.

Results are provided below in Tables 2 and 3:

TABLE 2

|  | Ac/Prop | |
| --- | --- | --- |
|  | PHB | PHV |
| E. coli LS5218 (p4A) | 21,000 | 0 |
| E. coli LS5219 (p4A) | 22,000 | 0 |
| E. coli LS5221 (p4A) | 37,000 | 0 |

TABLE 3

|  | Ac/Prop/Gluc | | | |
| --- | --- | --- | --- | --- |
|  | PHB | % | PHV | % |
| E. coli LS5218 (p4A) | 544,000 | 93 | 43,000 | 7 |
| E. coli LS5219 (p4A) | 27,000 |  | 0 |  |
| E. coli LS5221 (p4A) | 804,000 | 96 | 34,000 | 4 |

The above data show that at least 4–7% PHV (by weight, based on total PHB/V production), can be made by inducing acetate utilization genes in a bacterial host.

EXAMPLE 2

The effect of alterations of the acetate:propionate ratios on PHB/PHV production were evaluated in the following experiment. Briefly, a culture of E. coli LS5218 (p4A) was grown overnight in M9 Minimal Medium containing 10 mM acetate and 50 mM propionate. E. coli LS5218 (p4A) was inoculated into two cultures as follows: Culture A contained 40 mM acetate/10 mM propionate in M9, and Culture B contained 20 mM acetate/25 mM propionate in M9. Both cultures A and B were allowed to grow to late log phase, after which 0.4% glucose was added to each culture. After 48 hours, GC analysis (integration units) was performed as described above. Results are provided below in Table 4:

TABLE 4

| Culture A PHB = 267,000 (76%) | PHV = 85,000 (24%) |
| --- | --- |
| Culture B PHB = 16,000 (51%) | PHV = 154,000 (49%) |

The above data show that by altering the acetate/propionate ratios, the PHV concentration can be altered, and that nearly 50% PHV could be obtained.

EXAMPLE 3

Further, experiments were conducted by varying the acetate:propionate ratio in order to evaluate alterations in the ratio of PHB:PHV production. The experiments were performed essentially as described in Example 2, except that three strains of E. coli were utilized: E. coli LS5218 (p4A), LS5219 (p4A), LS5221 (p4A). The results of GC analysis (in integration units) for 40:10 and 20:25 ratios of acetate:propionate for days 1, 2, and 3, are set forth below in Tables 5 and 6, respectively:

TABLE 5

| 40 mM Ac/10 mM Prop | | | | |
| --- | --- | --- | --- | --- |
|  | PHB | % | PHV | % |
| Day 1 | | | | |
| E. coli LS5218 (p4A) | 259,000 | 76 | 80,000 | 24 |
| E. coli LS5219 (p4A) | 35,000 | 73 | 14,000 | 27 |
| E. coli LS5221 (p4A) | 54,000 | 100 | 0 | 0 |
| Day 2 | | | | |
| E. coli LS5218 (p4A) | 303,000 | 77 | 88,000 | 23 |
| E. coli LS5219 (p4A) | 43,000 | 69 | 19,000 | 31 |
| E. coli LS5221 (p4A) | 55,000 | 100 | 0 | 0 |
| Day 3 | | | | |
| E. coli LS5218 (p4A) | 371,000 | 76 | 114,000 | 24 |
| E. coli LS5219 (p4A) | 47,000 | 72 | 18,000 | 26 |
| E. coli LS5221 (p4A) | 54,000 | 100 | 0 | 0 |

TABLE 6

| 20 mM Ac/25 mM Prop | | | | |
| --- | --- | --- | --- | --- |
|  | PHB | % | PHV | % |
| Day 1 | | | | |
| E. coli LS5218 (p4A) | 143,000 | 52 | 134,000 | 48 |
| E. coli LS5219 (p4A) | 30,000 | 61 | 19,000 | 39 |
| E. coli LS5221 (p4A) | 23,000 | 77 | 7,000 | 23 |
| Day 2 | | | | |
| E. coli LS5218 (p4A) | 166,000 | 53 | 145,000 | 47 |
| E. coli LS5219 (p4A) | 36,000 | 61 | 23,000 | 39 |
| E. coli LS5221 (p4A) | 25,000 | 78 | 7,000 | 22 |

TABLE 6-continued 20 mM Ac/25 mM Prop

|  | PHB | % | PHV | % |
|---|---|---|---|---|
| Day 3 | | | | |
| E. coli LS5218 (p4A) | 174,000 | 53 | 157,000 | 47 |
| E. coli LS5219 (p4A) | 37,000 | 60 | 24,000 | 40 |
| E. coli LS5221 (p4A) | 525,000 | 69 | 11,000 | 31 |

From the experimental results provided above, it can be seen that an increase in propionate in the culture medium caused an increase in the production of PHV. The percentage of PHV production ranged from 0–30% (based on total percentage of PHB/V) for 40 mM Ac/10 mM Prop, to 20–50% for 20 mM Ac/25 mM Prop.

EXAMPLE 4

E. coli HMS174 (p4A) (ATCC Deposit No. 68329) was grown on a minimal medium containing whey into the late log phase, and then transferred into M9 medium containing 25 mM propionate. The culture was grown very slowly until an O.D.(600) of 0.3 was attained. At this time, 0.8% glucose was added. The culture was grown overnight, and a GC analysis was performed on culture. GC analysis showed 37,000 integration units for PHB, and 25,000 integration units for PHV. The percentage of PHB to PHV produced was about 60:40. Thus, PHV synthesis may be induced in any host which contains the acetate utilization pathway.

EXAMPLE 5

Strain LS5218 and HMS174(p4A) were inoculated from LB broth into various medium in order to determine whether acetate induction is necessary in order to produce both PHB and PHV. As can be seen from FIG. 11, acetate induction is not needed for E. coli LS5218 (which is constituitive for acetate utilization). Copolymer production in this strain is achieved by culturing the strain in a substrate having the preferred propionate:glucose ratios. However, acetate induction appears to be necessary in non-constituitive strains (e.g., HMS 174). In such a case, propionate in the substrate appears to be necessary for valerate production.

EXAMPLE 6

PHB/V was isolated and evaluated for its physical properties. Briefly, E. coli LS5218 (p4A) was grown as described above in Example 5. The resulting material was isolated by Soxhlet extraction, essentially as described by Preusting et al. in *Macromolecules* 23:4220–4224, 1990, except that methanol was utilized for precipitation rather than ethanol. The final material contained 84% PHB and 16% PHV. A solution cast film exhibited transparency and flexibility properties favorably comparable to a commercially available film made from a PHB-CoV copolymer obtained from A. eutrophus.

EXAMPLE 7

Various copolymers produced according to the above example were examined in order to determine whether valerate was present in the copolymer. The addition of valerate to the polymer causes a decrease in melting temperature of the polymer as measured by differential scanning calorimetry. A series of tests were run on polymers from different sources. Results are provided below in Table 7:

TABLE 7

| PHB* | Tm = 173.4° C. |
|---|---|
| PHB* | Tm = 173.15° C. |
| E. coli (PHB) | Tm = 174.6° C. |
| PHB/V (70/30)* | Tm = 116° C. |
| E. coli PHB/V (84/16) | Tm = 158° C. |

*commercially obtained from separate sources

The E. coli PHB/V copolymer (84/16) has decreased melting temperature, which corroborates the other data provided herein that the copolymer is PHB/V.

EXAMPLE 8

Figure 13A:
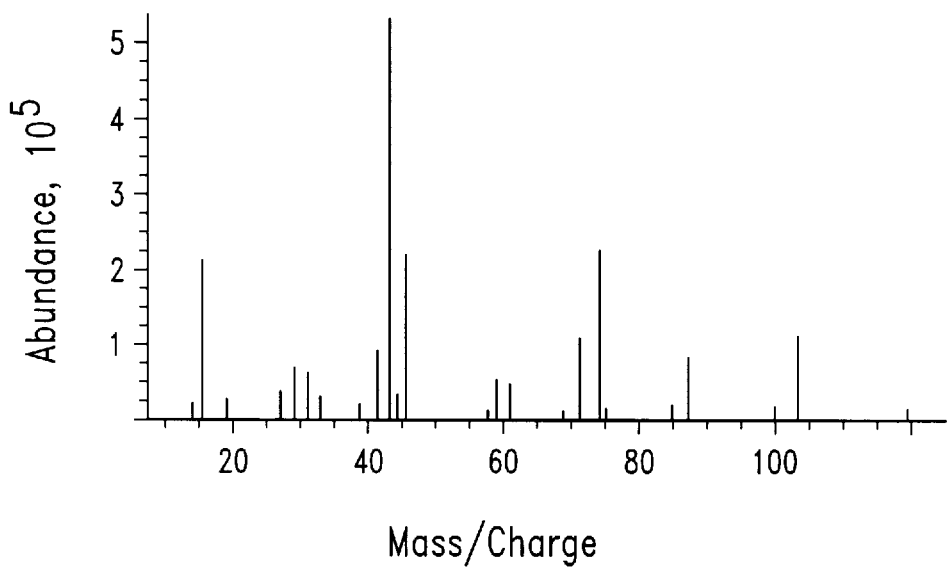
FIG. 13 is a series of graphs showing the gas chromatograph/mass spectrometer on purified PHB and PHV: graph A is a standard GC/MS of hydroxybutyrate; graph B is a standard GC/MS of hydroxyvalerate; graph C is the GC/MS of the PHB produced in Example 6; and, graph D is the GC/MS of the PHC produced in Example 6.
Figure 13B:
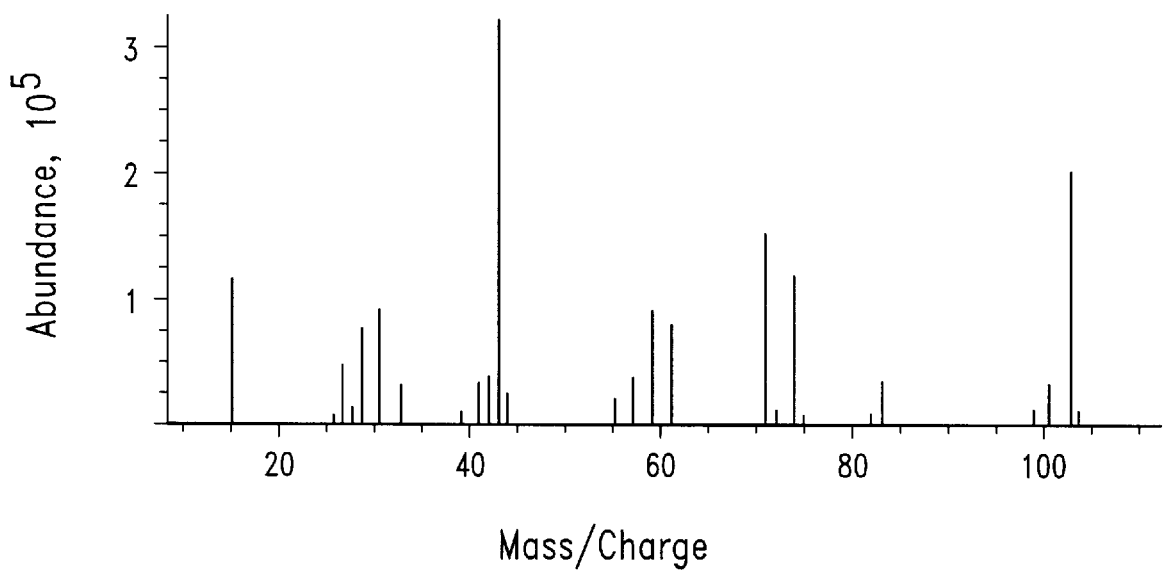
Figure 13C:
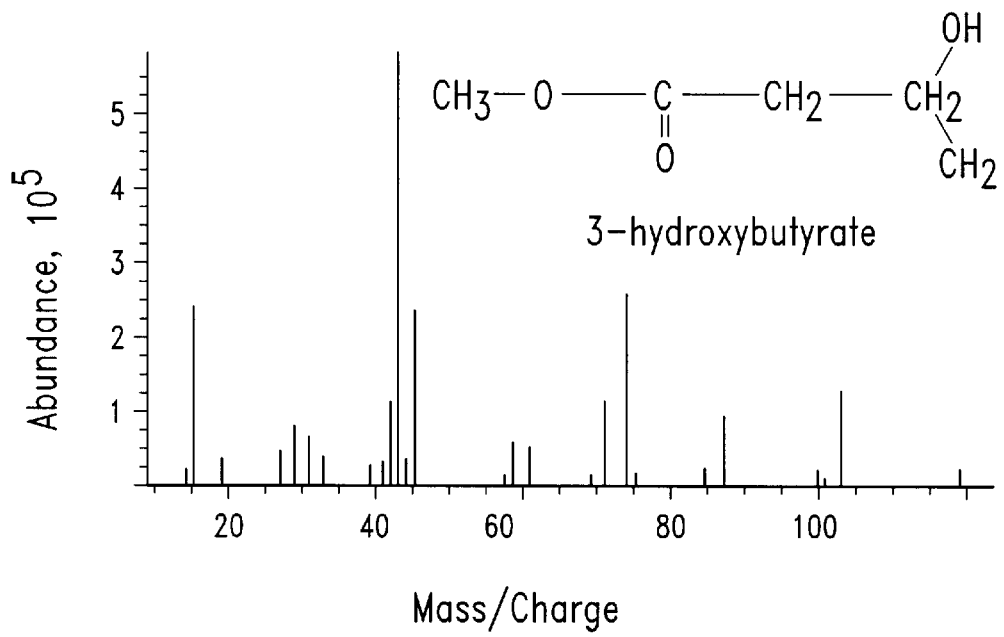
Figure 13D:
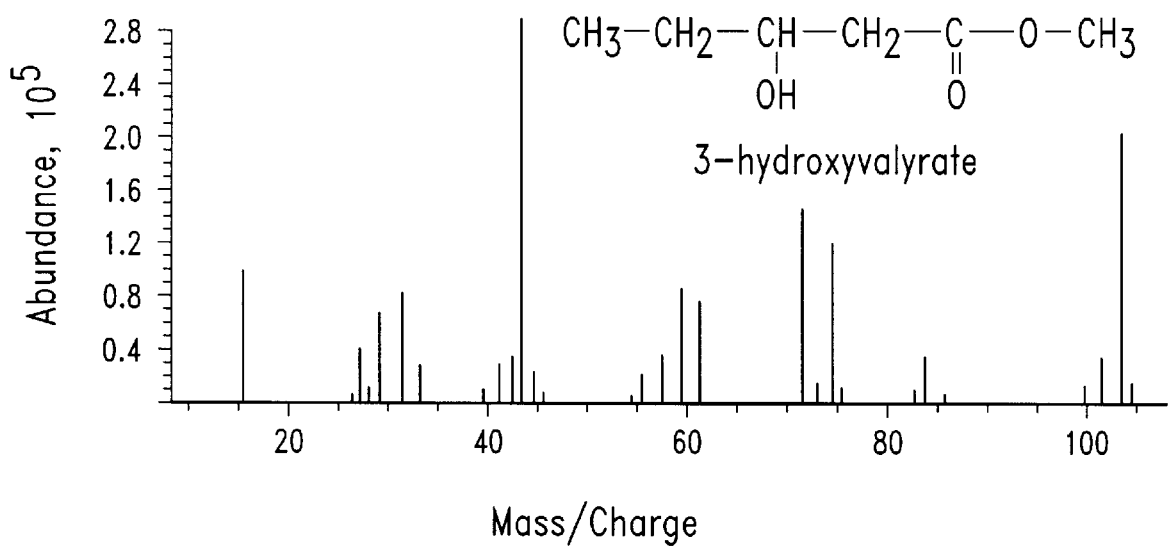

Mass spectrometry was performed on the PHB/V produced in Example 6. The results are shown in FIGS. 13A (3-HB) and 13B (3-HV). These chromatograms were compared to a known library (FIGS. 13C and 13D) in order to confirm that the peaks were in fact butyrate and valerate.

EXAMPLE 9

Copolymers of PHB and PHV were produced from a recombinant host cell which was stabilized with the recA protein. Briefly, E. coli LS5218 (p4A) was made recA using a P1 lysate that had been passed through a recA strain in order to allow for plasmid stability. The culture was grown in LB containing glucose, and then reinoculated into two cultures: Culture A contained minimal media and glucose, and Culture B contained minimal media and whey. When each culture reached an O.D.(600) of 0.8, propionate was added to 20 mM of each culture. The cultures were grown overnight and analyzed by GC as described above. Results are provided in Table 8:

TABLE 8

| Culture A PHB = 69,000 (79%) | PHV = 17,500 (21%) |
|---|---|
| Culture B PHB = 63,000 (89%) | PHV = 10,000 (11%) |

The E. coli LS5218 (p4A) recA still produces PHB/V. Prior acetate induction was not needed for this particular clone. A strain of this clone which was produced according to the techniques described above has been deposited with the American Type Culture Collection of 12301 Parklawn Drive, Rockville, Md., and bears Deposit No. ATCC 68681.

EXAMPLE 10

The E. coli LS5218 (p4A) recA strain was evaluated to determine whether alteration in the amount of propionate in the substrate alters the ratio PHB/V production. Briefly, the E. coli LS5218 (p4A) recA strain was grown overnight in LB containing 1% glucose. Eight 1 ml aliquots of this culture were utilized to innoculate eight 50 ml cultures containing M9 Minimal Medium and 1% glucose. These minimal cultures were grown to O.D.(600) of 0.8, then propionate at varying concentrations was added. Cultures were grown and samples taken for GC at 24 and 48 hours. The results are set forth below in Tables 9 and 10:

TABLE 9

At 24 hours

| Culture | O.D. | PHB | % | PHV | % |
|---|---|---|---|---|---|
| 0 mM Prop | 10.9 | 559,000 | 100 | 0 | 0 |
| 10 mM Prop | 10.7 | 470,000 | 65 | 247,000 | 35 |
| 20 mM Prop | 10.9 | 455,000 | 63 | 269,000 | 37 |
| 30 mM Prop | 12.1 | 432,000 | 61 | 270,000 | 39 |
| 40 mM Prop | 11.2 | 478,000 | 59 | 325,000 | 41 |
| 50 mM Prop | 10.9 | 487,000 | 63 | 288,000 | 37 |
| 100 mM Prop | 10.1 | 365,000 | 51 | 352,000 | 49 |
| 200 mM Prop | 1.8 | 0 | 0 | 0 | 0 |

TABLE 10

At 48 hours

| Culture | O.D. | PHB | % | PHV | % |
|---|---|---|---|---|---|
| 0 mM Prop | 10.9 | 540,000 | 100 | 0 | 0 |
| 10 mM Prop | 10.7 | 513,000 | 69 | 227,000 | 31 |
| 20 mM Prop | 11 | 441,000 | 63 | 256,000 | 37 |
| 30 mM Prop | 11.1 | 533,000 | 65 | 290,000 | 35 |
| 40 mM Prop | 10.9 | 535,000 | 63 | 310,000 | 37 |
| 50 mM Prop | 10.7 | 518,000 | 66 | 267,009 | 34 |
| 100 mM Prop | 10.1 | 299,000 | 50 | 298,000 | 50 |
| 200 mM Prop | 1.1 | 0 | 0 | 0 | 0 |

In the examples above it can be seen that an increase in the concentration of propionate in the substrate caused an increase in the production of PHV, which ranged from about 30–50%, based on the total percent of PHB/V produced.

EXAMPLE 11

E. coli LS5218(p4A) recA was inoculated into M9 media containing 25 mM acetate as a carbon source. The culture was grown overnight (as a 50 ml culture in a 250 ml shake flask) at 37° C. with shaking at 260 rpm. Two milliliters of the overnight culture was added to each of 6 flasks of M9 medium containing 20 mM acetate as carbon source. The bacterial cultures were grown at 37° C., 260 rpm shaking until the cultures reached an optical density (at 600 nm) of approximately 0.8 (about 8 hours). At this time, propionate was added to each flask such that the flasks had propionate levels of 2.5 mM, 5.0 mM, 7,5 mM, 10 mM, 20 mM, and 40 mM, respectively. The cultures were allowed to grow for another hour, and then glucose was added to a final concentration of 1%. The cultures were allowed to grow for another 20 hours as above, and then were harvested and analyzed by gas chromatography for the percentage of PHV. The results are set forth below in Table 11:

TABLE 11

| Culture | %PHB | %PHV |
|---|---|---|
| 2.5 mM Prop | 93 | 7 |
| 5.0 mM Prop | 91 | 9 |
| 7.5 mM Prop | 85 | 15 |
| 10 mM Prop | 90 | 10 |
| 20 mM Prop | 82 | 18 |
| 40 mM Prop | 76 | 24 |

Figure 12:
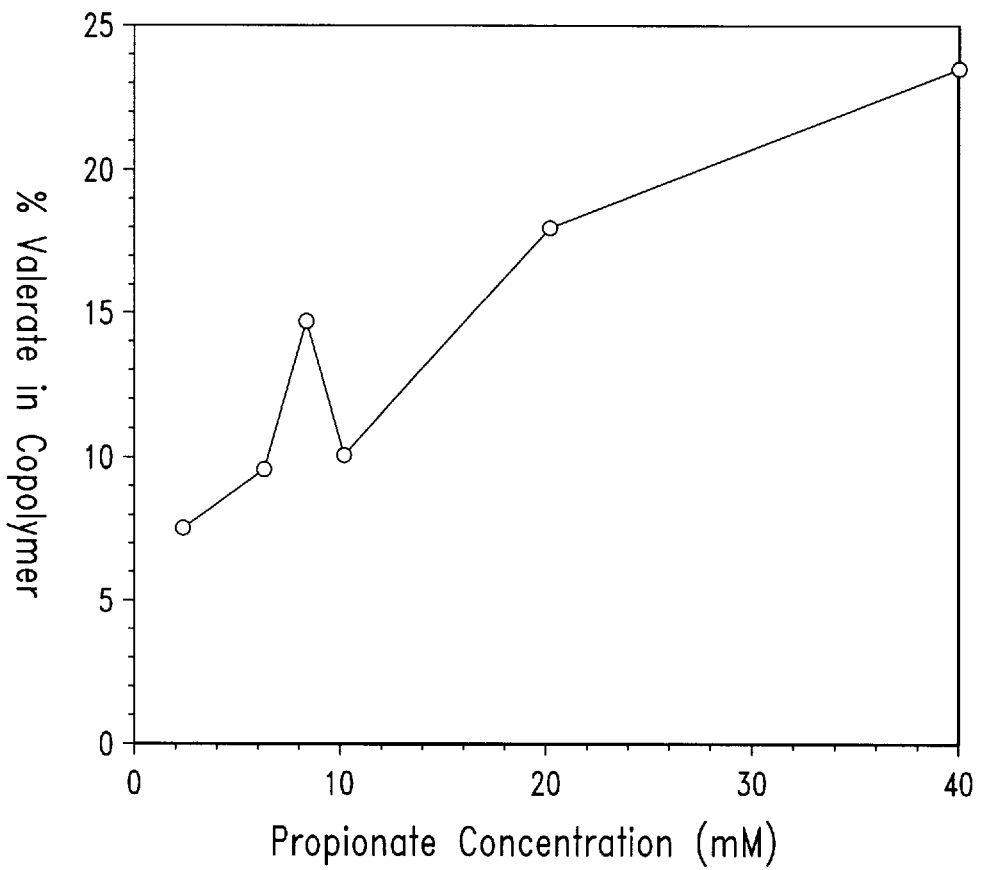
FIG. 12 is a graph showing valerate incorporation as a function of propionate concentration.

The data presented in FIG. 12 are the average results of 3 sets of experiments. The data show that PHV incorporation ranged from at least about 7% to about 25%, by weight. PHV is made even at relative low levels of propionate.

EXAMPLE 12

Comparison of P(HB-CO-V) Production in E. coli K12 and E. coli fadR atoC (CON)

The purpose of this experiment is to show that the fadR and atoC (Con) mutations may be utilized to synthesize copolymer in E. coli. Briefly, pJM9131 (see U.S. Ser. No. 5,569,595 [Attorney's Docket No. 910101.406], which is incorporated by reference herein in its entirety) was electroporated into E. coli K12 (wildtype, ATCC Deposit No. 53704) essentially as described above in Example 1. A clone producing PHA was selected from a Luria agar plate containing 1% glucose and 50 μg/ml kanamycin (on these indicator plates, colonies producing PHA are white compared to tan translucent colonies not producing PHA). pJM9131 was also electroporated into E. coli LS5218 (E. coli obtained from Dr. William Nunn's laboratory at the University of California, Irvine; see Spratt et al., Journal of Bacteriology 146:1166–1169; 1981). Isolated colonies of each strain on plates were inoculated into 3-ml LB cultures and incubated overnight in an orbital shaker at 225 rpm and 37° C. The next morning, 500 μl of the overnight culture was inoculated in 50-ml of LB containing 50 μg/ml kanamycin (250 ml baffled flasks), and grown at 37° C., 225 rpm, until the optical density at 600 nanometers reached between 0.8 and 1.2. Five milliliters of the culture was removed and centrifuged at 3,000 rpm for 15 minutes in a Heraeus Varifuge. The supernatant was aspirated, and the pellet resuspended in 5 ml of sterile 0.85% saline. Five-hundred microliters of this suspension was inoculated into 50 ml of M9 Minimal Medium containing 50 μg/ml kanamycin, 1% glucose and 10 mM sodium propionate, and the culture was grown at 37° C. and 225 rpm for 36 hours. Samples were the analyzed by gas chromatography for 3-hydroxybutyrate ("3-HB") and 3-hydroxyvalerate ("3-HV") accumulation as described above. Dry weight was also determined by removing 5 ml of culture to a preweighed 16×100 mm tube, centrifuging the tube in a Hereaeus Varifuge at 3,000 rpm for 15 min, and aspirating the supernatant. The pellet was then resuspended in 5 ml of 0.85% saline, and recentrifuged as above. The supernatant was again aspirated, and the tube containing the cell pellet was dried in a 55° C. incubator for several days. The tube was then removed, allowed to cool, and weighed. Dry weight was calculated by substrating the initial tube weight from the final weight of the tube containing the pellet.

Figure 17:
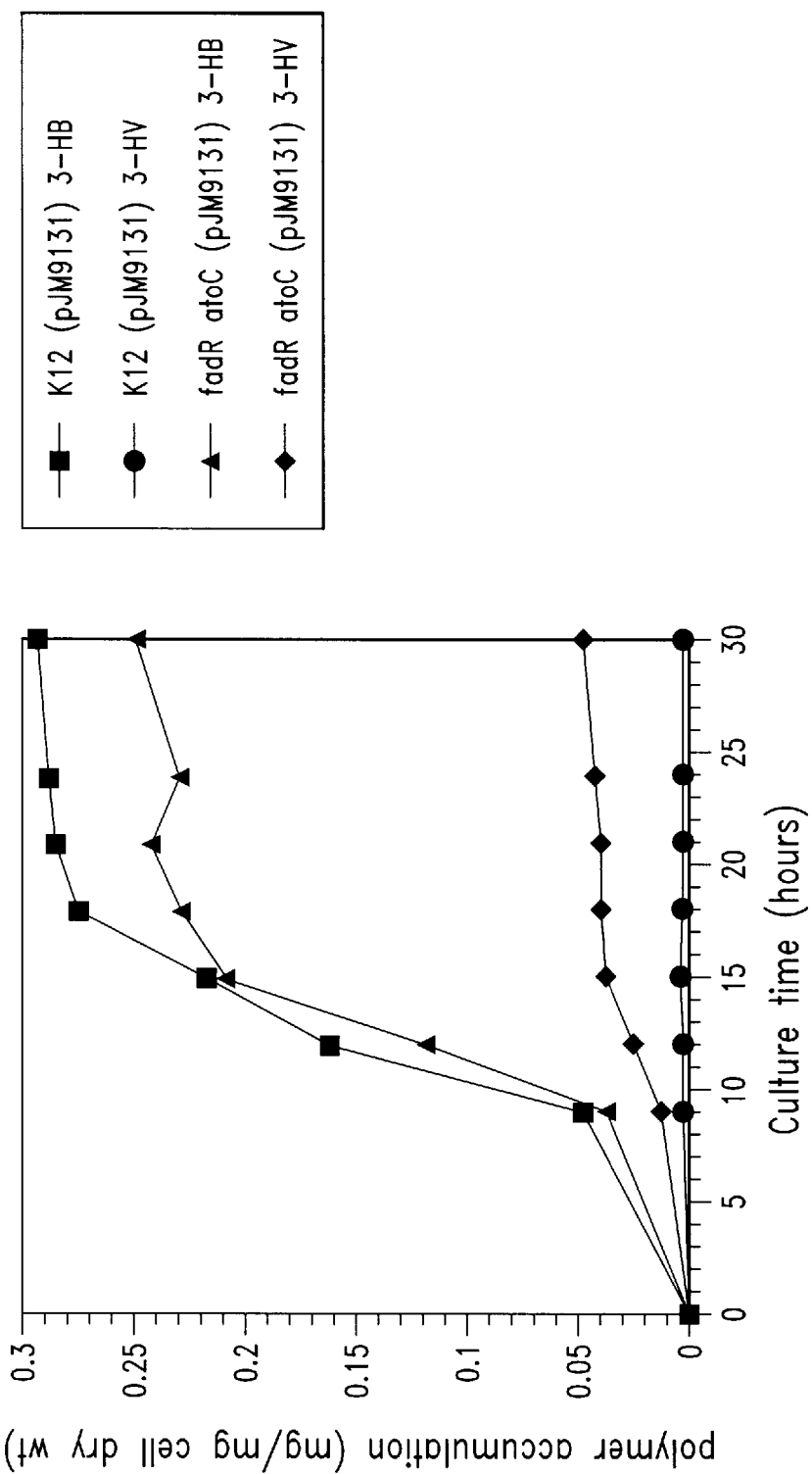
FIG. 17 is a graph which depicts PHA accumulation in K12 (pJM9131) and fadR atoC (pJM9131).

The results are shown in FIG. 17. Briefly, for each of the E. coli strains, PHA polymer accounted for approximately 30% of the cell dry weight. Of the total polymer produced in the E. coli wildtype strain, only 2 mol % represented 3-HV, whereas in the E. coli strain containing the fadR and atoC (Con) mutation, the total polymer was also approximately 30%, but the 3-HV content was 11 mol %, an increase of approximately 5-fold. Therefore, it is apparent that one or both of these mutations is instrumental in P(HB-co-V) formation.

EXAMPLE 13

Effect of the Art pta-ack Gene Products on P(HV-CO-V) Synthesis in fadR atoC (CON) Mutants Three stains, designated JMU 209, JMU 210, and JMU 222 were prepared using standard transduction techniques, as in "A Short Course in Bacterial Genetics" by Jeffrey Miller. (See Table 12 for specific strain designations.)

TABLE 12

Bacterial Strains

| Strain | Genotype | Reference or Derivation |
|---|---|---|
| K12 | Wild type | ATCC No. 53704 |
| LS5218 | fadR atoC (Con) | B.J. Bachman |
| BW16167 | Δ(his-gnd) 461 dhuA2pta-200 zej-223::Tn 10 | Wanner and Wilmes-Riesenberg |
| BW16168 | Δ(his-gnd) 461 dhuA2 Δ(pta-ackA-hisQ-hisP) zej-223::Tn 10 | Wanner and Wilmes-Riesenberg |
| JMU209 | fadR atoC Δ(pta-ackA) | P1(BW16169) × LS5218 |
| JMU210 | fadR atoC pta | P1(BW16167) × LS5218 |
| JMU222 | fadR atoC ackA | P1(BW16168) × LS5218 |

B. J. Bachman: Coli Genetic Stock Center, Yale University, New Haven, Conn. Wanner and Wilmes-Riesenberg: *J. Bacteriology* 174:2124–2130, 1992

Briefly, JMU 209 fadR atoC (Con) Δ(pta-ack) was prepared by transducing LS5218 fadR atoC (Con) with a transducing lysate of BW16169 (containing deletion in ack-pta genes). JMU 210 fadR atoC (Con) pta was prepared by transducing LS5218 fadR atoC (Con) with a traducing lysate of BW16167 (containing a pta mutation). JMU 222 fadR atoC (Con) ackA was prepared by transducing LS5218 fadR atoC (Con) with a transducing lysate of BW16168 (containing an ackA mutation). The three strains were analyzed to determined that they exhibited the correct phenotype (acetate kinase and phosphotransacetylase enzyme activity) essentially as described below. pJM913 1 was then introduced into these strains using electroporation as previously described, and strains producing PHA were selected on Luria agar plates containing 1% glucose and 50 μg/ml kanamycin as described above. Isolated colonies from each strain were selected, inoculated in 3-ml LB, and grown overnight at 37° C., 225 rpm. The next morning, 500 μl of the overnight culture was inoculated in 50-ml of LB containing 50 μg/ml kanamycin (250 ml baffled flasks), and grown at 37° C., 225 rpm, until the optical density at 600 nanometers reached between 0.8 and 1.2. Five ml of the culture was then removed and centrifuged at 3,000 rpm for 15 minutes in a Heraeus Varifuge. The supernatant was aspirated and the pellet resuspended in 5 ml of sterile 0.85% saline. Five-hundred microliters of this suspension was inoculated into 50 ml of M9 Minimal Medium containing 50 μg/ml kanamycin, 1% glucose, and 10 mM sodium propionate, and the culture was grown at 37° C., 225 rpm for approximately 24 hours. Samples were then collected, and assayed for acetate kinase activity (described below), phosphotransacetylase activity (described below), acetyl-CoA synthetase activity (described below), propionyl-CoA synthetase activity (described below), 3-hydroxybutyrate accumulation (as described above, sample collected at 36 hours), and 3-hydroxyvalerate accumulation (as described above, sample collected at 36 hours).

A. Preparation of bacterial cell lysates for enzymatic analyses

Bacterial cells were prepared for the enzymatic analyses described below in the following manner. Briefly, 10 ml of culture was pelleted by centrifugation at 3,000 rpm for 10 minutes in a Heraeus varifuge. The supernatant was aspirated and the pellet resuspended in ice-cold breaking buffer (10 mM potassium phosphate buffer (pH 7.2), 5 mM magnesium chloride, 1 mM ethylenediaminetetraacetic acid, 1 mM dithiothreitol, and 1M glycerol), and transferred to a 1.5 ml microcentrifuge tube on ice. The cell suspension (on ice) was then disrupted by sonication with an Fisher Sonic Dismembrator Model 300 (microtip) using four 15-second bursts, interspersed with 15-second cool-down periods. The crude extracts were then centrifuged in an Eppendorf Model 5415 microcentrifuge for 5 minutes. Supernatant was removed to new microcentrifuge tubes and placed on ice.

B. Measurement of Acetate Kinase

Acetate kinase levels were measured essentially according to the method described by Brown et al., *Journal of General Microbiology* 102:327–336; 1977. Briefly, reaction constituents (all from Sigma chemicals) were prepared, and added to a microcentrifuge tube as follows: 12.5 μl of 200 mM magnesium chloride, 50 μl of 100 mM ATP, 30 μl of 200 mM sodium acetate, 50 μl of hydroxylamine solution (see below), and 30 μl of water. All of these solutions except for magnesium chloride are made in 50 mM Tris buffer, pH 8.0. The tube was placed into a 37° C. dry block and equilibrated for 3 minutes. Next, 100 μl of diluted cell-free extract (dilutions range between 1:2 and 1:50) was added, the contents mixed, and the reaction allowed to proceed for 10 minutes. The reaction was stopped by adding 450 μl of ferric chloride reagent (see below), and the tube was placed on ice for 10 min. The tube was then centrifuged in a microcentrifuge for 2 min, and absorbance at 540 nanometers determined versus a blank containing all of the above constituents except for 100 μl of deionized water in place of the enzyme preparation.

The amount of acetyl-hydroxamate made (a measure of acetate kinase activity) was calculated by adding hydroxylamine solution to known amounts of acetyl phosphate (Sigma Chemicals) and generating a standard curve from the resulting spectrophotometer readings at 540 num. Proteins assays were done on the cell-free extract using the BioRad protein assay kit (BioRad Laboratories, Richmond Calif.). Final activities were calculated on the basis of micromole of acetyl hydroxamate formed per minute per mg of protein. (Hydroxlyamine reagent is made immediately before the assay by adding 0.5 ml of 4M hydroxylamine hydrochloride to 0.5 ml of 4M potassium hydroxide. Ferric chloride reagent is: 10% ferric chloride, 3.3% trichloroacetic acid, 0.66N hydrochloric acid.)

C. Measurement of Phosphotransacetylase

Phosphotransacetylase levels were measured essentially according to the method described by Brown et al. in *Journal of General Microbiology* 102:327–336; 1977. Briefly, reaction constituents (Sigma Chemical Company) were prepared and added to a microcuvette as follows: 100 μl of 1M Tris-HCl (pH8.0), 10 μl of 500 mM magnesium chloride, 100 μl of 5 mM NAD, 10 μl of 50 mM CoA, 10 μl of 500 mM L-malate, 10 μl of malic dehydrogenase (Sigma #M-9004), 10 μl of citrate synthase (Sigma #C-6987), 100 μl of 100 mM acetyl phosphate, and 550 μl of deionized water. The constituents were mixed, and placed in a Shimadzu UV-160 spectrophotometer (measuring at 340 nm) and zeroed against another cuvette containing the same constituents. The cuvette was removed, and 5 to 25 μl of cell-free extract was added to the cuvette. The cuvette was quickly mixed, and returned to the spectrophotometer. The change in absorbance at 340 nm was measured for approximately 30 seconds in order to calculate the change in absorbance per minute. This number was then divided by the extinction coefficient of NADH, 6.22 liter/mmol$^{-1}$ cm$^{-1}$, in order to calculate the mmol of NADH formed per minute. Protein assays were also performed as described above and the final specific activity was determined in units of μmoles NADH formed per minute, per mg of protein.

D. Measurement of Propionyl-CoA Synthetase Activity and Acetyl-CoA Synthetase Activity Propionyl-CoA synthetase activity and acetyl-CoA synthetase activity were measured using a slight modification of the method described by Krahenbuhl and Brass (Biochemical Pharmacology, Vol 41, No. 6/7, pp. 1015–23, 1991. Briefly, reaction constituents (Sigma Chemical Company) were prepared and added to a microcentrifuge tube as follows: 25 µl of 0.5 M/50 mM Hepes-KOH buffer (pH 8.0), 2.5 µl 5 mM magnesium chloride, 5 µl of 2 mM ATP, 12.5 µl of 0.05 mM CoA, 12.5 µl of 0.5 mM DTT, 25 µl of cell-free lysate, and 117.5 µl of deionized water. The constituents were mixed and placed in a 37° C. heat block for 2 minutes. Next 50 µl of $^{14}$C-propionyl-CoA (DuPont, NEC-093H) was added to the tube, and mixed. At 1, 3, and 5 minutes, 20 µl samples were removed from the tube and placed on Whatman filter paper disks (GF/F, Baxter Scientific) pinned to a styrofoam board. After the reaction was completed, all the filters were placed in a beaker (on ice) containing 300 ml ethanol, 100 ml diethyl ether, 1 ml trichloroacetic acid. The contents of the beaker was gently stirred every 6 minutes, for a total of 60 minutes, and washed with the same solution for a period of 5 minutes (with constant gentle stirring). The filter was then washed with 200 ml of diethyl ether for 5 minutes (on ice). The filters were removed with forceps, and dried on aluminum foil. The filters were placed in scintillation vials with 5 ml of scintillation fluid (Scintiverse; Fisher Scientific), and counted in a Beckman LS5000TA liquid scintillation counter. Based upon the specific activity of the radiolabeled propionate and the protein concentration, the specific activity may be determined in units of nanomole of product formed per min per milligram of protein.

The acetyl-CoA synthetase assay may be performed in essentially the same manner, except that $^{14}$C-acetyl-CoA was substituted for $^{14}$C-propionyl-CoA.

As shown in FIG. 18, there is relationship between ackipta activity and 3-HV incorporation into the copolymer. In particular, in the ack or pta mutants, 3-HV incorporation drops approximately 5-fold. Therefore, these genes are instrumental in 3-HV incorporation into the copolymer.

EXAMPLE 14

Effect of ackA Overproduction of 3-HV Incorporation into P(HB-CO-HV)

The purpose of this experiment was to demonstrate that overproduction of the ack gene product could increase the percentage of 3-HV in the copolymer. Briefly, the ack gene was obtained from A. Nakata (Lee et al., *Journal of Bacteriology* 172:2245–2249; 1990) on plasmid pMKU814. This plasmid is a pUC derivative with a 1.4 kb fragment that contains the ack gene from the *E. coli* chromosome. A plasmid containing the PHB biosynthesis genes and the ack gene was constructed by removing the ack gene from pMKU on a 1.4 kb EcoR I-Pst I fragment, filling in the 5' overhangs utilizing the Klenow procedure (Maniatis, et al.) and ligating the filled-in fragment into pJM9131 that had been digested with Dra I (blunt-ended cut).

The recombinant plasmid was introduced into *E. coli* DH5 alpha by electroporation. Possible recombinant clones were screened for the presence of the correct plasmid construct by alkaline lysis minipreps, followed by diagnostic restriction endonuclease digests and agarose gel electrophoresis (Maniatis, et al.). A clone having the correct vector construct (designated pJM9350) was selected, and large-scale plasmid preparations were performed in order to obtain workable amounts of pJM9350. The plasmid was introduced into JMU222 fadR atoC (Con) ackA, JMU 209 fadR atoC (Con) Δ(pta-ack), and LS5218 fadR atoC (Con) by electroporation as previously described. Isolated colonies on plates were inoculated into 3-ml LB cultures, and grown overnight at 37° C., 225 rpm. The next morning, 500 µl of the overnight culture was inoculated in 50 ml of LB containing 50 µg/ml kanamycin (250 ml baffled flasks), and grown at 37° C., 225 rpm, until the optical density at 600 nanometers reached between 0.8 and 1.2. Five milliliters of the culture was removed and centrifuged at 3,000 rpm for 15 minutes in a Heraeus Varifuge. The supernatant was aspirated, and the pellet resuspended in 5 ml of sterile 0.85% saline. Five-hundred microliters of this suspension was inoculated into 50 ml of M9 Minimal Medium containing 50 µg/ml kanamycin, 1% glucose, and 10 mM sodium propionate, and the culture was grown at 37° C., 225 rpm. After approximately 24 hours, samples were taken for analysis of acetate kinase activity (described above), phosphotransacetylase activity (described above), acetyl-CoA synthetase activity (described above), propionyl-CoA synthetase activity (described above), 3-hydroxybutyrate, and 3-hydroxyvalerate accumulation (described above).

Results are shown in FIG. 19. In particular, strain JMU 222, containing a mutation in the ack gene, was clearly complemented by the presence of the ack gene on the multicopy plasmid. In comparison to FIG. 18, the same strain which previously was able to make only 1.4% 3-HV, was able to incorporate 3-HV at levels approximating 23% of the total polymer. In addition, as shown in FIG. 19 the function of the pta gene was necessary because complementation does not occur in a pta- background. Finally, it can be seen that even LS5218 (wildtype for ack and pta) experiences a significant increase in 3-HV incorporation (compared to FIG. 18).

EXAMPLE 15

Demonstration of an Alternate System for Propionate Incorporation into P(HB-CO-HV).

*E. coli* JMU 209fadR atoC (Con) Δ(ack-pta) was selected from a Luria agar plate and inoculated into 3 ml of LB overnight at 37° C., 225 rpm. The next morning, 500 µl of the overnight culture was inoculated in 50-ml of LB containing 50 µg/ml kanamycin (250 ml baffled flasks), and grown at 37° C., 225 rpm, until the optical density at 600 nanometers reached between 0.8 and 1.2. Five milliliters of the culture was removed and centrifuged at 3,000 rpm for 15 minutes in a Heraeus Varifuge. The supernatant was aspirated and the pellet resuspended in 5 ml of sterile 0.85% saline. Five-hundred microliters of this suspension was inoculated into 50 ml of M9 Minimal Medium containing 50 µg/ml kanamycin and 10 mM sodium propionate, and the culture was grown at 37° C., 225 rpm. After 48 hours of growth, the optical density at 600 nm had reached 0.4. At this time glucose was added to a final concentration of 1%. Growth was allowed to continue for 22 hours.

Figure 20:
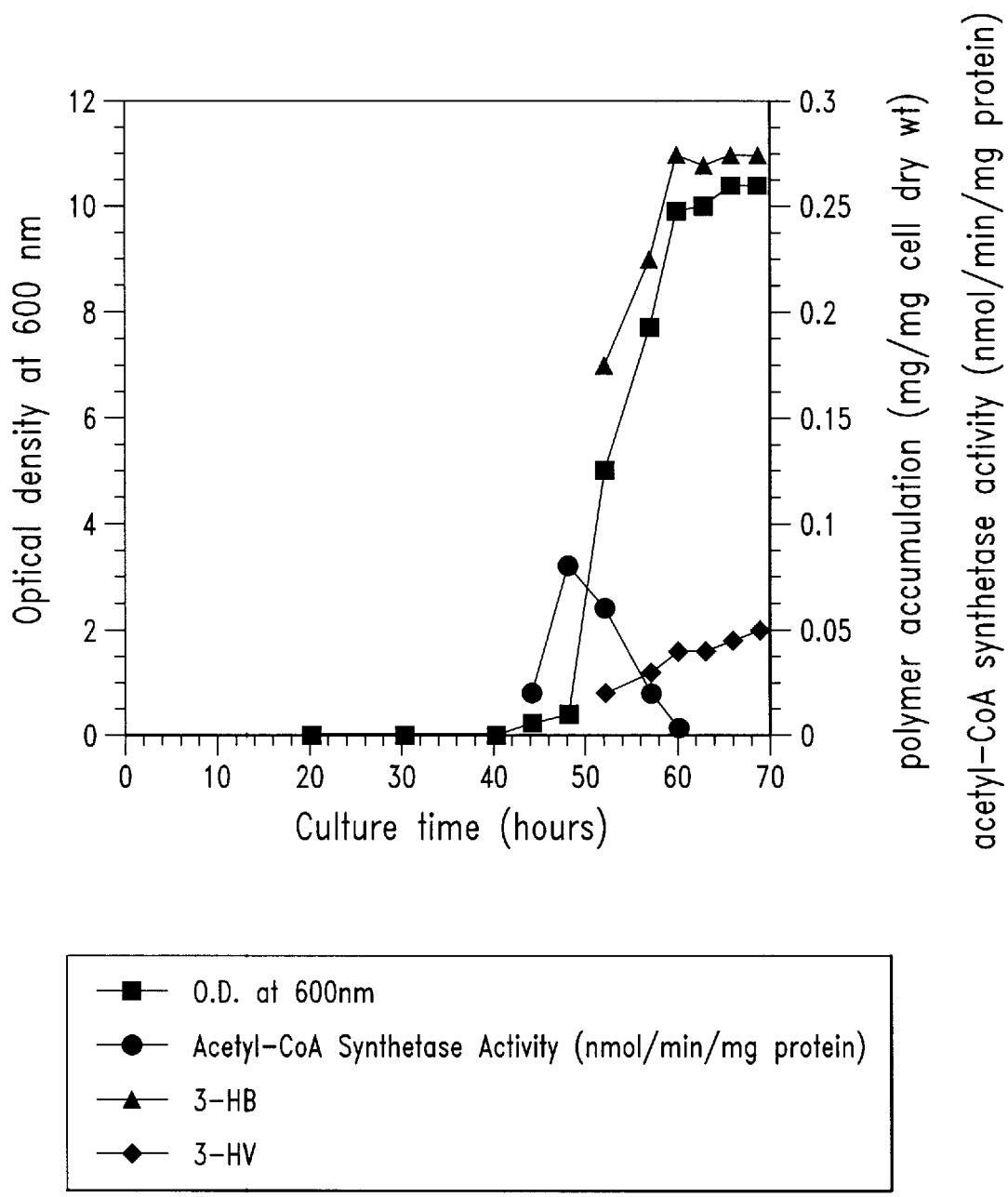
FIG. 20 is a graph which depicts $OD_{600}$, Acetyl-CoA Synthetase Activity, 3-HB and 3-HV production.

During the first 48 hours of culture only the optical density at 600 nm was assayed. After glucose addition, samples were taken at various time intervals and analyzed for acetyl-CoA synthetase activity, 3-HB incorporation, 3-HV incorporation, optical density, dry weight analysis (described above) and propionyl-CoA synthetase activity as described above. The results are shown in FIG. 20. Briefly, the total polymer accumulation reached 28% of the dry well weight, and commenced upon the addition of glucose to the culture. 3-HV was accumulated to a final concentration of approximately 20 mol %. Acetyl-CoA synthetase activity was severely depressed upon the addition of glucose. Propionyl-CoA synthetase activity was not measurable in this system.

The results indicate that there is an inducible acetyl-CoA synthetase that is different from the ack/pta system. Furthermore, it appears to be repressed by glucose. Since the ack/pta system was inactivated, and no propionyl-CoA activity was detected, it is not known how 3-HV was incorporated into the polymer. It is speculated that there is an additional metabolic pathway for the synthesis of propionyl-CoA operative at this time. In may even be that the enzymes of fatty acid oxidation are so highly expressed in this situation that there were significant amounts of propionyl-CoA in the cell that originated from odd-chain fatty acid degradation.

EXAMPLE 16 pta/ack Mutants are Unable to Accumulate Significant Amounts of 3-HV

Because the above experimented indicated that copolymer can be made even in the absence of the ack/pta system, the following experiment was designed to show that under the conditions that are normally used to obtain copolymer (glucose present at beginning of culture), pta/ack mutants are unable to incorporate 3-HV.

JMU209 fadR atoC (Con) (pJM9131) was grown in 3-ml of LB+50 µg/ml kanamycin overnight at 37° C., 225 rpm. The next morning, 500 µl of the overnight culture was inoculated in 50-ml of LB containing 50 µg/ml kanamycin (250 ml baffled flasks), and grown at 225 rpm and 37° C., until the optical density at 600 nanometers reached between 0.8 and 1.2. Five milliliters of the culture was removed and centrifuged at 3,000 rpm for 15 minutes in a Heraeus Varifuge. The supernatant was aspirated, and the pellet resuspended in 5 ml of sterile 0.85% saline. Five-hundred microliters of this suspension was inoculated into 50 ml of M9 Minimal Medium containing 50 µg/ml kanamycin, 1% glucose and 10 mM sodium propionate, and the culture was grown at 37° C., 225 rpm, for 24 hours. Samples were taken at time intervals for analysis of 3-HB incorporation, and 3-HV incorporation, dry weight, and acetyl-CoA synthetase activity as described herein.

Figure 21:
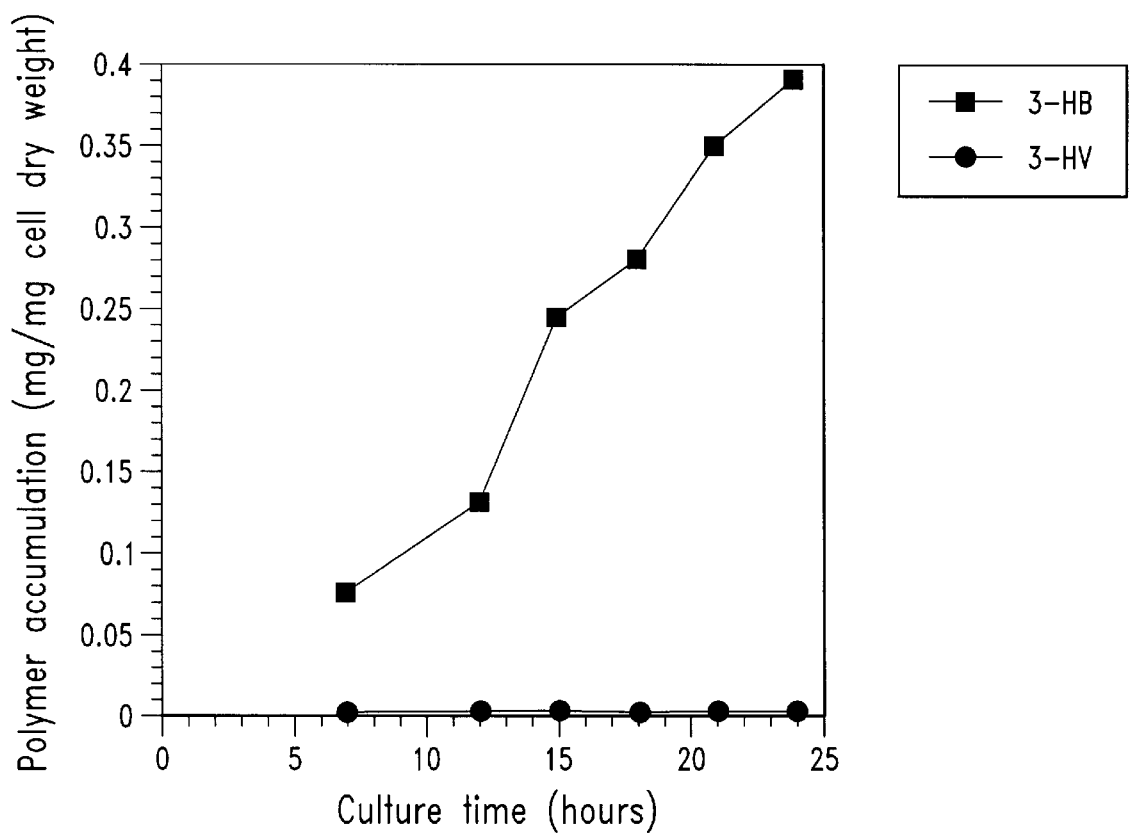
FIG. 21 is a graph which depicts total polymer accumulation (3-HB and 3-HV) for JMU209 fadR atoC (Con) (pJM9131).

The results are shown in FIG. 21. Briefly, the total polymer reached 40% of the cell dry weight. The level of 3-HV incorporated into this polymer was below the limits of detection. Likewise, no acetyl-CoA synthetase activity was detected. This supports the theory that the alternate acetyl-CoA synthetase is inducible (repressed by glucose) and is somehow responsible for 3-HV incorporation.

EXAMPLE 17 atoC Can Independently Cause the Production of P (HB-co-V) COPOLYMER.

All ato constructs and strains used in the following experiments are set forth below in Table 13:

TABLE 13

Bacterial Strains

| Strain | Genotype | Reference or Derivation |
|---|---|---|
| K12 | Wild type | ATCC No. 53704 |
| LS5218 | fadR 601 atoC2 | B.J. Bachman |
| LJ14 | fadR 601 atoC 512 atoD 32 | B.J. Bachman |
| LJ32 | fadR 601 atoC 512 atoD 32 | B.J. Bachman |
| RS3242 | trpE61 Tna-5dad R1, trpA62 zef-117::Tn10 | B.J. Bachman |
| RS3032 | Lambda purB58,fadR613::Tn | B.J. Bachman |
| CAG18516 | MG1655 zef-3114::Tn10kan | C.A. Gross |
| CAG18544 | MG1655 fadR 3115::Tn10 | C.A. Gross |
| JMU171 | fadR::Tn10 atoC | P1(RS3032) × LS5218 |
| JMU172 | zef-3114::Tn10 kan atoC | P1(CAG18516) × JMU171 |
| JMU173 | zef-117::Tn10 atoC | P1(RS3032) × JMU172 |
| JMU187 | fadR::Tn10kan atoC 512 atoA 514 | P1(CAG18544) × LJ14 |
| JMU188 | fadR::Tn10kan atoC 512 atoD 32 | P1(CAG18544) × LJ32 |
| JMU189 | zef-117::Tn10 atoC 512 atoA 514 | P1(RS3242) × JMU187 |
| JMU190 | zef-117::Tn10 atoC 512 atoD 32 | P1(RS3242) × JMU188 |

B. J. Bachman: Coli Genetic Stock Center, Yale University, New Haven, Conn. C. A. Gross: Department of Bacteriology, University of Wisconsin, Madison, Wis.

Strains constructed through P1 transduction were done so employing the techniques outlined in "A Short Course in Bacterial Genetics" by Jeffrey Miller.

E. coli K12 and E. coli JMU173 atoC (Con) were selected from Luria agar plates and inoculated into 3-ml LB containing 50 µg/ml kanamycin cultures, and grown overnight at 37° C., 225 rpm. The next morning, 500 µl of the overnight culture was inoculated in 50-ml of LB containing 50 µg/ml kanamycin (250 ml baffled flasks), and grown at 37° C., 225 rpm, until the optical density at 600 nanometers reached between 0.8 and 1.2. Five ml of the culture was removed and centrifuged at 3,000 rpm for 15 minutes in a Heraeus Varifuge. The supernatant was aspirated, and the pellet resuspended in 5 ml of sterile 0.85% saline. Five-hundred microliters of this suspension was inoculated into 50 ml of M9 Minimal Medium containing 50 µg/ml kanamycin, 1% glucose and 10 mM sodium propionate, and the culture was grown at 37° C., 225 rpm for 30 hours. Samples were taken at time intervals and analyzed for 3-HB accumulation (described in CIP), 3-HV accumulation (described in CIP), and cell dry weight (described above).

Figure 22:
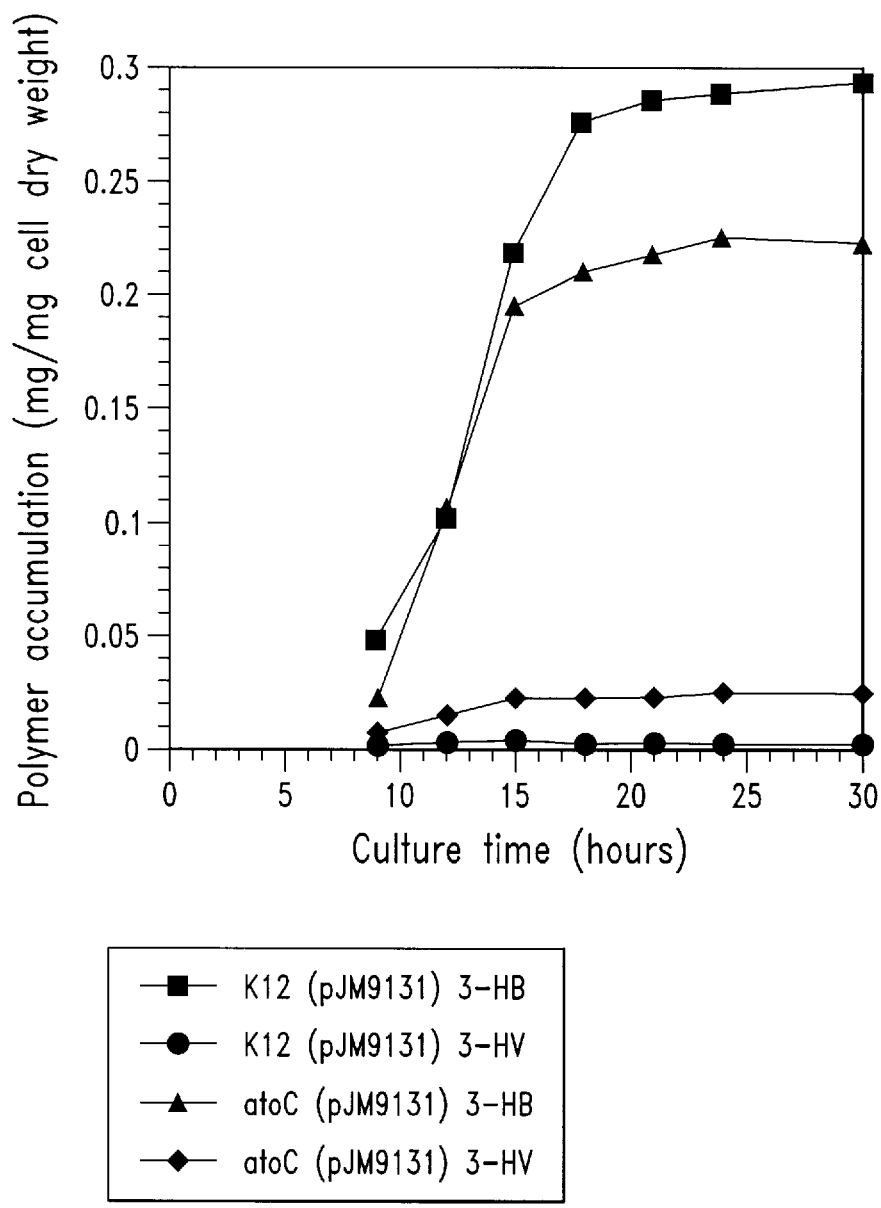
FIG. 22 is a graph which depicts 3-HB and 3-HV accumulation for K12 (pJM9131) and atoC (pJM9131).

The results are shown in FIG. 22. Briefly, E. coli K12 accumulated polymer up to 30% of its cell dry weight. However, only 2 mol % of this was 3-HV. On the other hand, E. coli JMU173 atoC (Con) accumulated polymer to 23% of the cell dry weight and 10% of the polymer was 3-HV. This indicates that the atoC (Con) mutation promotes the incorporation of 3-HV into copolymer.

EXAMPLE 18

The Function of atoC (CON) Mutations is to Cause Increase in the Uptake of Propionate and Acetate.

E. coli K12 and E. coli JMU173 atoC (Con) (isolated colonies on an Luria agar plate) were grown overnight at 37° C., 225 rpm, in 50-ml of M9 Minimal Medium containing 1% glucose, 10 mM propionate, and 50 µg/ml kanamycin. The next morning, 5 ml of these cultures were centrifuged at 3,000 rpm for 15 minutes in a Heraeus varifuge. The supernatant was aspirated, and the pellet resuspended in 5 ml of 0.85% NaCl. Five hundred microliters of this suspension was inoculated into 50 ml M9 Minimal Medium containing 1% glucose and 10 mM propionate, and grown at 37° C. to late log phase. The entire culture was harvested by centrifugation at 3,000 rpm for 15 minutes in a Heraeus varifuge, and the resulting pellet was washed twice with carbon-free M9 medium. The final pellet was resuspended in carbon-free M9 medium to give a final optical density at 600 nm of 2.0. Five hundred microliters of this suspension was placed into a 13×100 mm test tube, and preincubated for 10 minutes at 37°. $^{14}$C-propionate (20 nmole) was added to the suspension, and 40 µl samples were removed at intervals and filtered through a 0.45 µm membrane (Millipore Corporation). The membrane was then rinsed three times with 3 ml of carbon-free M9 Minimal Medium. The filters were dried at room temperature, added to scintillation vials containing 5 ml Scintiverse (Fisher Scientific), and counted in a Beckman LS5000TA scintillation counter.

Figure 23:
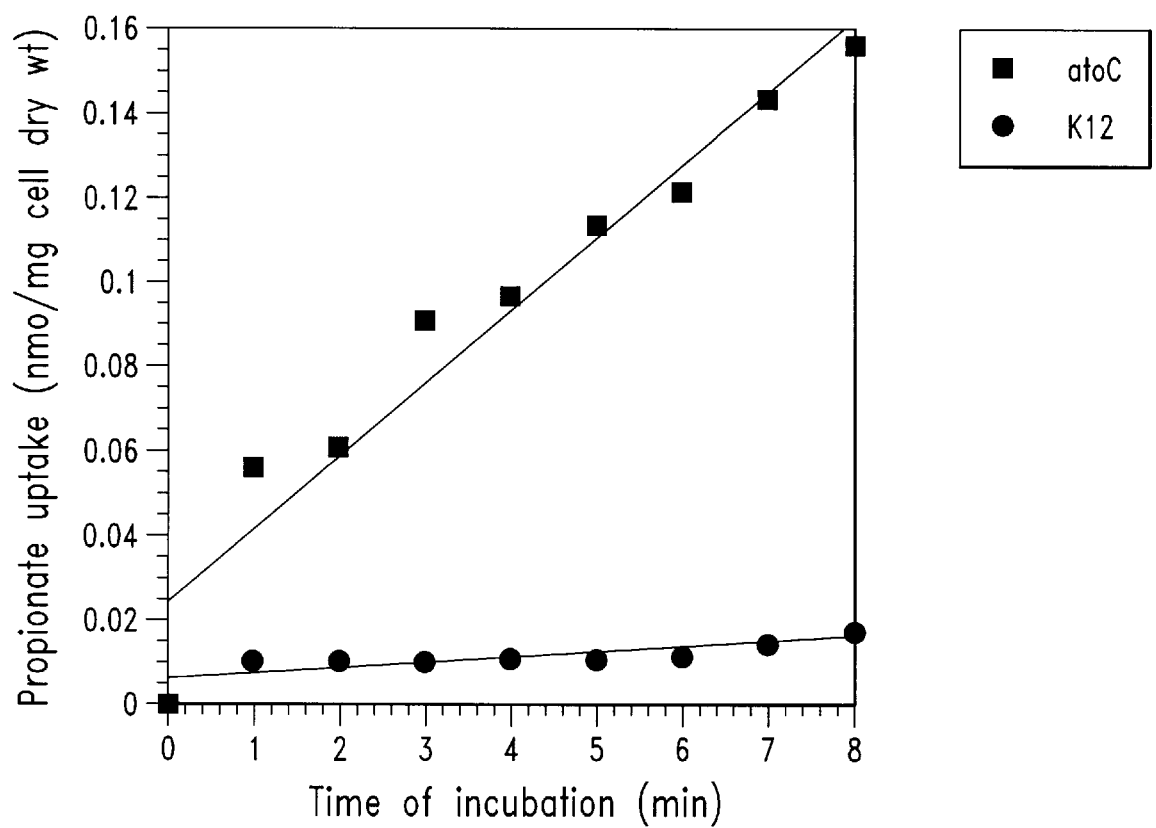
FIG. 23 is a graph which depicts propionate uptake for JMU173 atoC (Con) and K12.

The results are shown in FIG. 23. In particular, uptake is expressed as nanomole propionate taken up per mg cell dry weight. E. coli JMU 173 atoC (Con) takes up propionate approximately 10 times as fast as E. coli K12. This increase in uptake probably accounts for the increase in 3-HV incorporation, since, as shown above, enzymes necessary to convert propionate to propionyl-CoA, acetate kinase and phosphotransacetylase, are constituitively expressed.

EXAMPLE 19

The ato Structural Genes atoD and atoA Must be Functional in Order for atoC (CON) Mutants to be Effective.

Strains used in this experiment are E. coli K12, E. coli JMU173 atoC (Con), E. coli JMU189 atoC (Con) atoA 514, and E. coli JMU190 atoC (Con) atoD 32 (See Table 13). New strains used in this experiment (JMU189 and JMU190) were constructed by P1 transduction as specified above.

Isolated colonies of the above strains were inoculated into 3 ml LB containing 50 µg/ml kanamycin, and grown overnight at 37° C., 225 rpm. The next morning, 500 µl of the overnight culture was inoculated in 50-ml of LB containing 50 µg/ml kanamycin (250 ml baffled flasks), and grown at 37° C., 225 rpm, until the optical density at 600 nanometers reached between 0.8 and 1.2. Five milliliters of the culture was removed and centrifuged at 3,000 rpm for 15 minutes in a Heraeus Varifuge. The supernatant was aspirated, and the pellet resuspended in 5 ml of sterile 0.85% saline. Five-hundred microliters of this suspension was inoculated into 50 ml of M9 Minimal Medium containing 50 µg/ml kanamycin, 1% glucose and 10 mM sodium propionate, and the culture was grown at 37° C., 225 rpm for 36 hours. At this time samples were taken for analysis of 3-HB incorporation, 3-HV incorporation, cell dry weight, and propionate uptake as described above.

The results are shown in FIG. 24. In particular, the results indicate that the structural protein atoD is necessary for efficient uptake of propionate and efficient production of 3-HV. atoD mutants do not take up propionate any faster than K12 strains, and only produce slightly larger amounts of 3-HV. In contrast, uptake in E. coli JMU173 atoC (Con) is much higher.

EXAMPLE 20

Induction of the ATO System

Strains used in this experiment were E. coli K12, E. coli JMU173 atoC (Con) and E. coli JMU190 atoC (Con) atoD (See Table 13, above). Isolated colonies of the above strains were inoculated into 3 ml LB containing 50 µg/ml kanamycin, and grown overnight at 37° C., 225 rpm. The next morning, 500 µl of the overnight culture was inoculated into 50-ml of LB containing 50 µg/ml kanamycin (250 ml baffled flasks), and grown at 37° C., 225 rpm, until the optical density at 600 nanometers reached between 0.8 and 1.2. Five milliliters of the culture was removed and centrifuged at 3,000 rpm for 15 minutes in a Heraeus Varifuge. The supernatant was then aspirated and the pellet resuspended in 5 ml of sterile 0.85% saline. Five-hundred microliters of this suspension was inoculated into 50 ml of M9 Minimal Medium containing 50 µg/ml kanamycin, 20 mM sodium acetate, and 10 mM sodium propionate, and the culture was grown at 37° C., 225 rpm until late log phase. The entire culture was harvested by centrifugation at 3,000 rpm for 15 minutes in a Heraeus varifuge and the resulting pellet was washed twice with carbon-free M9 medium. The final pellet was resuspended in carbon-free M9 medium to give a final optical density at 600 nm of 2.0. Five hundred microliters of this suspension was placed into a 13×100 mm test tube and preincubated for 10 minutes at 37°. $^{14}$C-propionate (20 nmole) was added to the suspension and 40 µl samples were removed at intervals, and filtered through a 0.45 µm membrane (Millipore Corporation). The membrane was then rinsed three times with 3 ml of carbon-free M9 Minimal Medium. The filters were dried at room temperature, added to scintillation vials containing 5 ml Scintiverse (Fisher Scientific), and counted in a Beckman LS5000TA scintillation counter.

Figure 25:
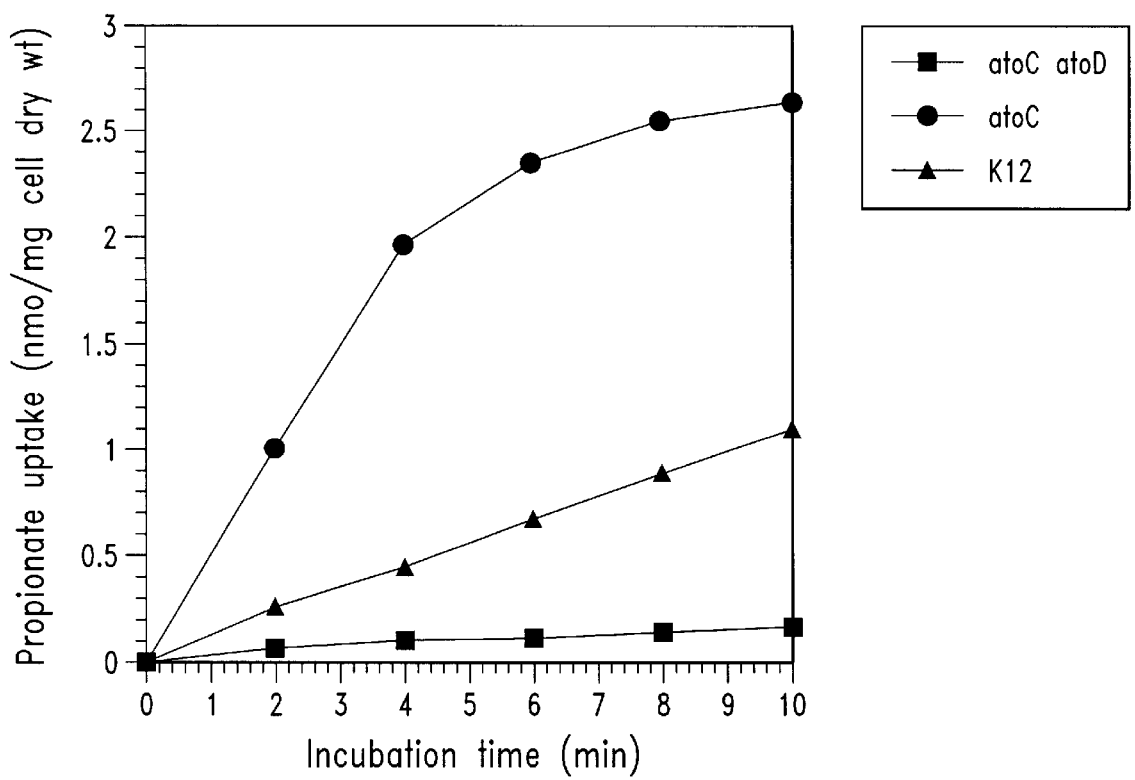
FIG. 25 is a graph which depicts propionate uptake levels in K12, JMU173 atoC (Con), and JMU190 atoC (Con) atoD.

Results are shown in FIG. 25. In particular, both E. coli K12 and E. coli JMU173 are induced to considerable uptake levels. However, JMU173 appears to be twice as high. On the other hand, no significant induction was seen in JMU190 atoC (Con) atoD, indicating that the induction seen in the other strains is probably due to the ato system.

EXAMPLE 21

Catabolic Repression of the ato System

Strains used in this experiment were E. coli K12 and E. coli JMU173 atoC (Con) and E. coli JMU190 atoC (Con) atoD (See Table 13, above). Isolated colonies of the above strains were inoculated into 3 ml LB containing 50 ml kanamycin and grown overnight at 37° C., 225 rpm. The next morning 500 µl of the overnight culture was inoculated in 50 ml of LB containing 50 µg/ml kanamycin (250 ml baffled flasks), and grown at 37° C., 225 rpm, until the optical density at 600 nanometers reached between 0.8 and 1.2. Five milliliters of the culture was removed and centrifuged at 3,000 rpm for 15 minutes in a Heraeus Varifuge. The supernatant was aspirated and the pellet resuspended in 5 ml of sterile 0.85% saline. Five-hundred microliters of this suspension was inoculated into 50 ml of M9 Minimal Medium containing 50 µg/ml kanamycin, 20 mM sodium acetate, 10 mM sodium propionate, and 1% glucose. In addition, another 500 microliters of cell suspension was inoculated into separate 50 ml cultures containing the same medium and 5 mM cAMP. The cultures were grown at 37° C., 225 rpm until late log phase. The entire culture was harvested by centrifugation at 3,000 rpm for 15 minutes in a Heraeus varifuge, and the resulting pellet was washed twice with carbon-free M9 medium. The final pellet was resuspended in carbon-free M9 medium to give a final optical density at 600 nm of 2.0. Five hundred microliters of this suspension was placed into a 13×100 mm test tube, and preincubated for 10 minutes at 37° C. $^{14}$C-propionate (20 nmole) was added to the suspension, and 40 μl samples were removed at intervals and filtered through a 0.45 μm membrane (Millipore Corporation). The membrane was then rinsed three times with 3 ml of carbon-free M9 Minimal Medium. The filters were dried at room temperature, added to scintillation vials containing 5 ml Scintiverse (Fisher Scientific), and counted in a Beckman LS5000TA scintillation counter.

Figure 26A:
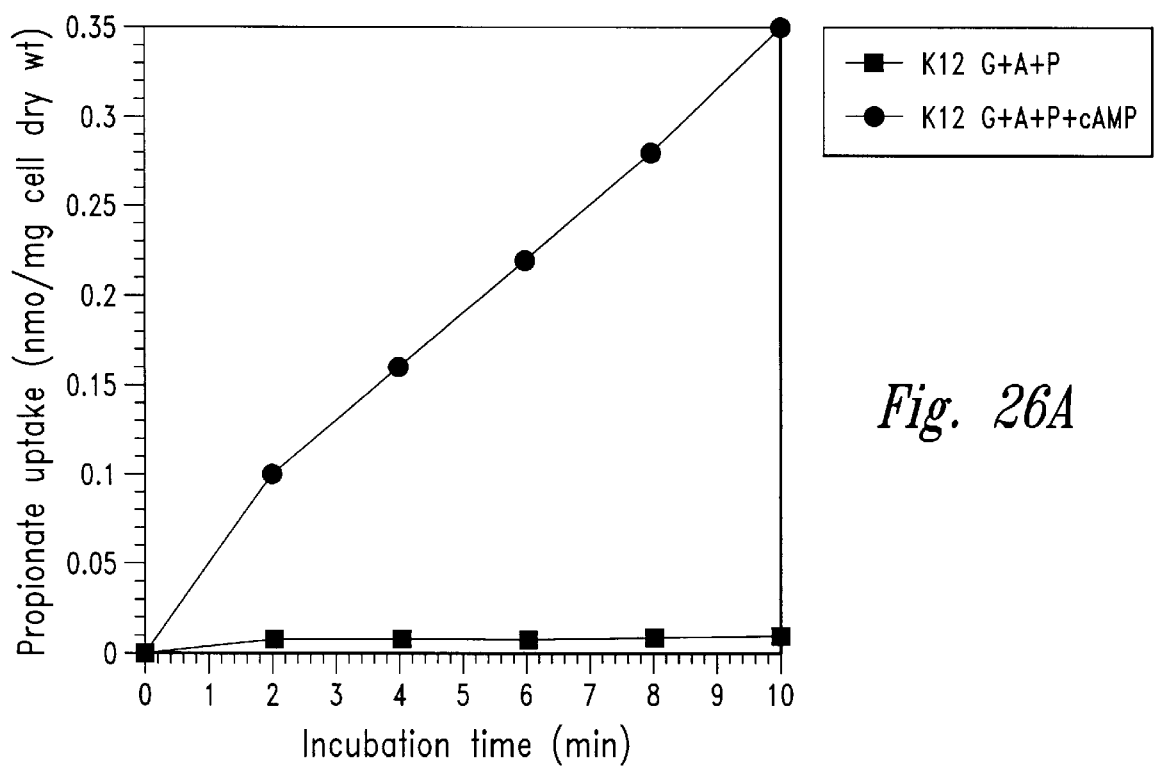
FIG. 26A and 26B are two graphs which depict propionate uptake in K12 (FIG. 26A) and atoC (FIG. 26B).
Figure 26B:
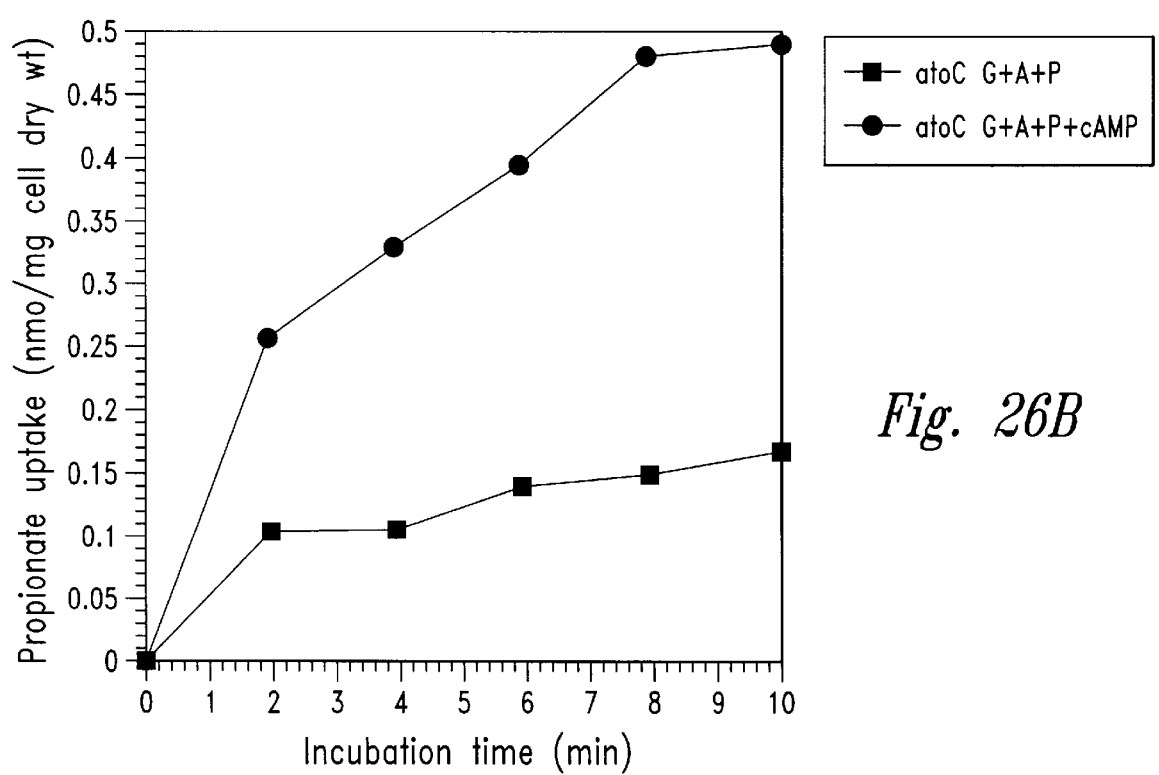

Results are shown in FIG. 26. In particular, in the presence of acetate/propionate/glucose, uptake of propionate in K12, JMU173, and JMU190 was catabolically repressed. No significant increase in propionate cpm was observed. However, when cAMP was added to the same cultures, all strains experienced increased uptake of propionate. The highest increase was in the atoC (Con) strain, JMU173, but even the strain having the atoD mutation, JMU190, also experienced an increase. These results indicate that the ato system is catabolically repressed.

EXAMPLE 22

The fadR Mutation Can Work Independently of the atoC Mutation.

Strains used within this example are set forth below in Table 14. Strains constructed by P1 transduction were done using methods previously described.

TABLE 14

Bacterial Strains

| K12 | Wild type | ATCC No. 53704 |
| RS3032 | Lambda purB58fadR::Tn10 | B.J. Bachman |
| LS5218 | fadR 601 atoC2 | B.J. Bachman |
| LS6590 | fadB 64 | P.N. Black |
| LS6591 | fadA 30 | P.N. Black |
| pN109 | ΔfadL fadR | P.N. Black |
| JMU170 | fadR::Tn10 | P1(RS3032) × K12 |
| JMU192 | fadR::Tn10 ΔfadL | P1(RS3032) × pN109 |
| JMU193 | fadR::Tn10 fadB 64 | P1(RS3032) × LS6590 |
| JMU194 | fadR::TN10 fadA 30 | P1(RS3032) × LS56591 |

B. J. Bachman: Coli Genetic Stock Center, Yale University, New Haven, Conn. P. N. Black: Dept. of Biochemistry, University of Tennessee, Memphis, Tenn.

Strains used in this experiment included E. coli JMU 170 fadR (pJM9131) and E. coli LS5218fadR, atoC (Con) (pJM9131). The strains were selected as isolated colonies on Luria agar plates (containing 50 μg/ml kanamycin), and grown in 3-ml LB cultures (containing 50 μg/ml kanamycin) overnight at 37° C., 225 rpm. In the morning, the bacterial cells were pelleted by centrifugation at 3,000 rpm for 10 minutes in a Heraeus varifuge. The supernatant was aspirated, and the pellet resuspended in 3 ml of M9 Minimal Medium. One milliliter of each culture was used to inoculate each of 7 separate flasks containing 50 ml of M9 Minimal Medium, 50 μg/ml kanamycin, 1% glucose, and propionate at a final concentration of either 0, 2.5, 5, 7.5, 10, 15, or 20 mM (these seven concentrations represent the seven different flasks). The cultures (250-mi baffled flasks) were grown at 37° C., 225 rpm, for approximately 30 hours, and then samples were taken for analysis of 3-HB and 3-HV accumulation (as described above). These values were utilized to calculate the amount of 3-HV accumulation as a total of the percentage polymer.

Figure 27:
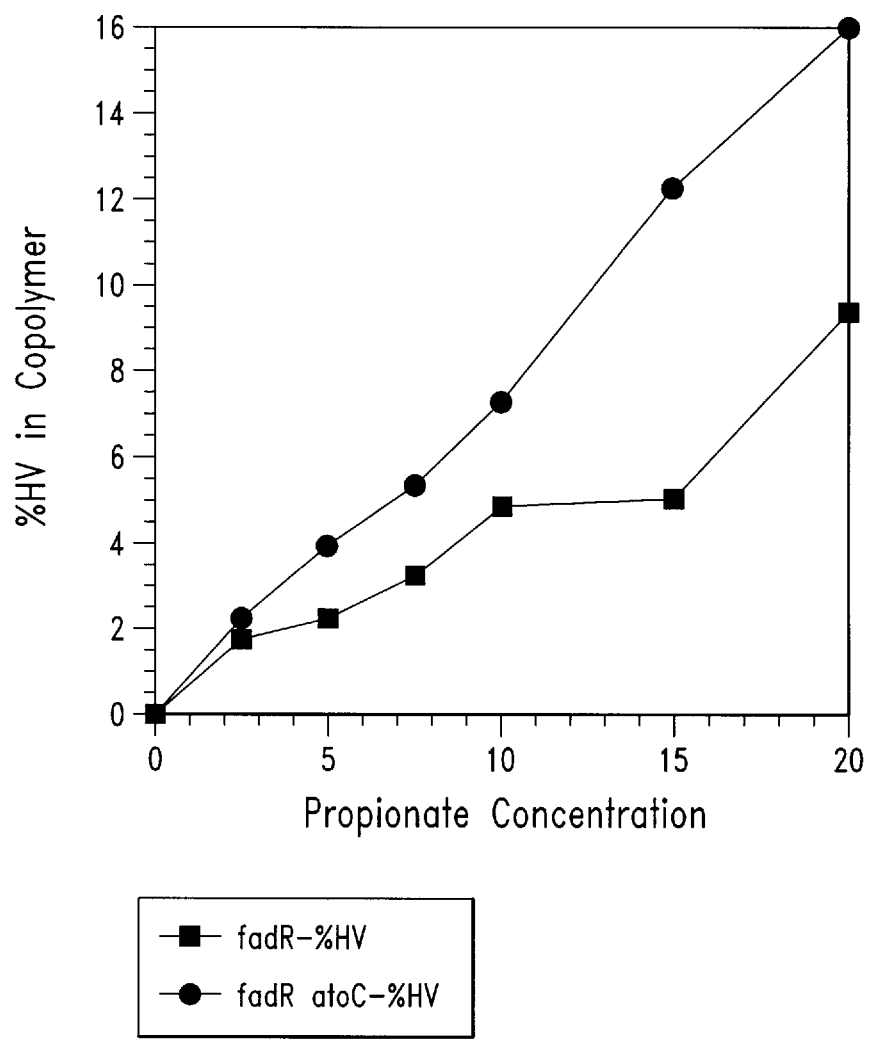
FIG. 27 is a graph which depicts the percentage of HV in copolymer at various concentrations of propionate.

Results are shown in FIG. 27. The E. coli strain containing the fadR mutation was able to accumulate significant amounts of 3-HV. At 10 mM propionate concentration the 3-HV percentage was approximately 5 mol % whereas at 20 mM propionate concentration the 3-HV content was approximately 9 mol %. Therefore, increasing the propionate concentration in the medium increases the final 3-HV percentage of the polymer. Additionally, it can be seen that the addition of the atoC (Con) mutation to the strain causes an increase in polymer percentage that is approximately double what would be obtained via the fadR mutation alone. For instance, at 10 mM propionate the 3-HV is 5 mol % for the fadR strain, and 8 mol % for the fadR atoC (Con) strain. Similarly, at 20 mM propionate, the 3-HV content is 9 mol % for the fadR strain, and 16 mol % for the fadR atoC (Con) strain.

EXAMPLE 23

The Structural Genes of the fad System

Strains used in this experiment were constructed or obtained as specified in Table 14 above. Strains used included E. coli JMU170 fadR, E. coli JMU192 fadR fadL, E. coli JMU193 fadR fadB, and E. coli 194 fadR fadA. The fadL gene is instrumental in long chain fatty acid transport The fadA and fadB genes are enzymes of the fatty acid oxidation system. The purpose of this experiment was to determine whether any of these fad system gene products are instrumental in production of copolymer by fadR mutants.

The above strains were selected as isolated colonies from LB plates, and were grown in 3-ml of LB containing 50 μg/ml kanamycin overnight at 37° C., 225 rpm. The next morning 500 μl of the overnight culture was inoculated in 50 ml of LB containing 50 μg/ml kanamycin (250 ml baffled flasks), and grown at 37° C., 225 rpm, until the optical density at 600 nanometers reached between 0.8 and 1.2. Five milliliters of the culture was removed and centrifuged at 3,000 rpm for 15 minutes in a Heraeus Varifuge. The supernatant was aspirated, and the pellet resuspended in 5 ml of sterile 0.85% saline. Five hundred microliters of this suspension was inoculated into 50 ml of M9 Minimal Medium containing 50 μg/ml kanamycin, 1% glucose, and 10 mM sodium propionate, and the culture was grown at 37° C., 225 rpm for 36 hours. Samples were taken for analysis of 3-HB and 3-HV incorporation (described above).

Results are shown in FIG. 28. Briefly, the gas chromatography results indicate that the fad structural genes play an important role in copolymer and polymer formation. Interestingly, the fadL mutation appears to have the effect of increasing the 3-HB content dramatically, while decreasing the 3-HV content only slightly. On the other hand, the fadA and fadB mutations cause a substantial reduction of total polymer, and result in no accumulation of 3-HV.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method for the production of poly-β-hydroxyalkanoate copolymer, comprising:

(a) introducing into a prokaryotic host cell selected from the group consisting of Nocardiaceae, Streptomycetaceae, Pseudomonadaceae, Corynebacteria, Citrobacter, Klebsiella, Serratia, Zymomonas and Flavobacterium a vector construct which directs the expression of a nucleic acid molecule which encodes a poly-β-hydroxybutyrate biosynthetic pathway;

(b) introducing into said host cell a vector construct which directs the expression of one or more proteins selected from the group consisting of atoC, atoD, fadAB, pta and ack which regulate acetate and propionate metabolism;

(c) culturing said host cell in medium containing propionate; and (d) isolating poly-β-hydroxyalkanoate copolymer from said cultured host cell.

2. A method for the production of poly-β-hydroxyalkanoate copolymer, comprising:

(a) introducing into a prokaryotic host cell selected from the group consisting of Nocardiaceae, Streptomycetaceae, Pseudomonadaceae, Corynebacteria, Citrobacter, Klebsiella, Serratia, Zymomonas and Flavobacterium a vector construct which directs the co-expression of a nucleic acid molecule which encodes a poly-β-hydroxybutyrate biosynthetic pathway, and one or more proteins selected from the group consisting of atoC, atoD, fadAB, pta and ack which regulate acetate and propionate metabolism;

(b) culturing said host cell in medium containing propionate; and (c) isolating poly-β-hydroxyalkanoate copolymer from said cultured host cell.

3. A method for the production of poly-β-hydroxyalkanoate copolymer, comprising:

(a) introducing into a prokaryotic host cell selected from the group consisting of Nocardiaceae, Streptomycetaceae, Pseudomonadaceae, Corynebacteria, Citrobacter, Klebsiella, Serratia, Zymomonas and Flavobacterium which produces poly-β-hydroxybutyrate a vector construct which directs the expression of one or more proteins selected from the group consisting of atoC, atoD, fadAB, pta and ack which regulate acetate and propionate metabolism;

(b) culturing said host cell in medium containing propionate; and (c) isolating poly-β-hydroxyalkanoate copolymer from said cultured host cell.

4. The method of claims 1, 2 or 3 wherein said protein is encoded by an atoC (Con) mutant.

5. The method of claims 1, 2 or 3 wherein said protein is encoded by ackA.

6. The method of claims 1, 2 or 3 wherein said protein is encoded by pta.

7. A host cell selected from the group consisting of Nocardiaceae, Streptomycetaceae, Pseudomonadaceae, Corynebacteria, Citrobacter, Klebsiella, Serratia, Zymomonas and Flavobacterium which contains a vector construct which directs the expression of a sequence which encodes a poly-β-hydroxybutyrate biosynthetic pathway, and a vector construct which directs the expression of one or more proteins selected from the group consisting of atoC, atoD, fadAB, pta and ack which regulate acetate and propionate metabolism.

8. A host cell selected from the group consisting of Nocardiaceae, Streptomycetaceae, Pseudomonadaceae, Corynebacteria, Citrobacter, Klebsiella, Serratia, Zymomonas and Flavobacterium which contains a vector construct which directs the co-expression of a sequence which encodes a poly-β-hydroxybutyrate biosynthetic pathway, and one or more proteins selected from the group consisting of atoC, atoD, fadAB, pta and ack which regulate acetate and propionate metabolism.

9. A method for the production of poly-β-hydroxyalkanoate copolymer, comprising:

(a) introducing into a prokaryotic host cell selected from the group consisting of Nocardiaceae, Streptomycetaceae, Pseudomonadaceae, Corynebacteria, Citrobacter, Klebsiella, Serratia, Zymomonas and Flavobacterium a vector construct which directs the expression of a nucleic acid molecule which encodes a poly-β-hydroxybutyrate biosynthetic pathway, said host cell being one or more of a fadR or atoC (Con) mutant;

(b) culturing said host cell in medium containing propionate; and (c) isolating poly-β-hydroxyalkanoate copolymer from said cultured host cell.

10. A method for the production of poly-β-hydroxyalkanoate copolymer, comprising:

(a) culturing a prokaryotic host cell which produces poly-β-hydroxybutyrate, wherein said host cell is selected from the group consisting of Nocardiaceae, Streptomycetaceae, Pseudomonadaceae, Corynebacteria, Citrobacter, Klebsiella, Serratia, Zymomonas and Flavobacterium, and wherein said host cell is one or more of a fadR or atoC (Con) mutant; and (b) isolating poly-β-hydroxyalkanoate copolymer from said cultured host cell.

11. The method of claims 1, 2, 3, 9 or 10 wherein said host cell is *Klebsiella oxytoca*.

12. The method of claims 1, 2, 3, 9 or 10 wherein said host cell is *Klebsiella aerogenes*.

13. The method of claims 1, 2, 3, 9 or 10 wherein said host cell is *P. fluorescens*.

14. The method of claims 1, 2 or 3 wherein said protein is encoded by atoC.

* * * * *